United States Patent
Lutteropp et al.

(10) Patent No.: US 11,033,619 B2
(45) Date of Patent: *Jun. 15, 2021

(54) COMBINATION OF IMMUNE EFFECTOR CELLS SPECIFIC FOR A TARGET ANTIGEN AND HEMATOPOIETIC CELLS THAT EXPRESS THE TARGET ANTIGEN IN AN ALTERED FORM

(71) Applicant: Miltenyi Biotec GmbH, Bergisch Gladbach (DE)

(72) Inventors: Michael Lutteropp, Bergisch Gladbach (DE); Anne Richter, Bergisch Gladbach (DE); Andrew Kaiser, Bergisch Gladbach (DE); Mario Assenmacher, Bergisch Gladbach (DE); Stefan Miltenyi, Bergisch Gladbach (DE)

(73) Assignee: MILTENYI BIOTEC B.V. & CO. KG, Gladbach (DE)

( * ) Notice: Subject to any disclaimer, the term of this patent is extended or adjusted under 35 U.S.C. 154(b) by 133 days.

This patent is subject to a terminal disclaimer.

(21) Appl. No.: 16/005,466

(22) Filed: Jun. 11, 2018

(65) Prior Publication Data
US 2018/0280502 A1    Oct. 4, 2018

Related U.S. Application Data

(62) Division of application No. 14/952,448, filed on Nov. 25, 2015, now Pat. No. 10,201,606.

(30) Foreign Application Priority Data

Nov. 26, 2014   (DE) ................... 1020142240719

(51) Int. Cl.
*A61K 39/395* (2006.01)
*A61K 38/17* (2006.01)
*A61K 39/00* (2006.01)
*A61K 35/12* (2015.01)

(52) U.S. Cl.
CPC ......... *A61K 39/3955* (2013.01); *A61K 35/12* (2013.01); *A61K 38/1774* (2013.01); *A61K 39/0005* (2013.01); *A61K 2035/124* (2013.01); *A61K 2039/5156* (2013.01)

(58) Field of Classification Search
CPC ............... A61K 39/3955; A61K 35/12; A61K 38/1774; A61K 39/0005
See application file for complete search history.

(56) References Cited

U.S. PATENT DOCUMENTS

| | | | |
|---|---|---|---|
| 10,137,155 B2 | 11/2018 | Mukherjee et al. | |
| 10,201,606 B2 | 2/2019 | Lutteropp et al. | |
| 10,548,922 B2 | 2/2020 | Gill et al. | |
| 2012/0309091 A1 | 12/2012 | Ando et al. | |
| 2016/0144026 A1 | 5/2016 | Lutteropp et al. | |

FOREIGN PATENT DOCUMENTS

| | | |
|---|---|---|
| EP | 2711418 A1 | 3/2014 |
| EP | 3025719 B1 | 9/2018 |
| EP | 3105317 B1 | 9/2018 |
| WO | 2012012667 | 1/2012 |
| WO | 2014059173 | 4/2014 |
| WO | 2017066760 A1 | 4/2017 |
| WO | 2017079400 A1 | 5/2017 |

OTHER PUBLICATIONS

Anurathapan et al., Engineered T cells for cancer treatment, Cytotherapy, vol. 16, 2014, pp. 713-733.
De Oliveira et al., "Modification of hematopoietic stem/progenitor cells with CD19-specific chimeric antigen receptors as a novel approach for cancer immunotherapy", Human Gene Therapy, vol. 24, No. 10, Oct. 2013, pp. 824-839.
EP15196309, "European Search Report", dated Feb. 17, 2016, 2 pages.
Hinrichs et al., "Reassessing target antigens for adoptive T-cell therapy", Nature Biotechnology, vol. 31, No. 11, Oct. 20, 2013, pp. 999-1008.
Lamers et al., "Treatment of metastatic renal cell carcinoma with CAIX CAR-engineered T cells: clinical evaluation and management of on-target toxicity", Mol Ther., vol. 21, No. 4, Apr. 2013, pp. 904-912.
Leisegang et al., "MHC-restricted fratricide of human lymphocytes expressing survivin-specific transgenic T cell receptors", J Clin Invest., vol. 120, No. 11, Nov. 2010, pp. 3869-3877.
Morgan et al., "Case Report of a Serious Adverse Event Following the Administration of T Cells Transduced With a Chimeric Antigen Receptor Recognizing ERBB2", Mol Ther., vol. 18, No. 4, Apr. 2010, pp. 843-851.
Morgan et al., "Recognition of glioma stem cells by genetically modified T cells targeting EGFRvIII and development of adoptive cell therapy for glioma", Human Gene Therapy, vol. 23, No. 10, Oct. 2012, pp. 1043-1053.
National Cancer Institute, "CAR T-Cell Therapy: Engineering Patients' Immune Cells to Treat Their Cancers", available online at http://www.cancer.gov/aDout-cancer/treatment/researcn/car-t-cens, May 18, 2015, 6 pages.

(Continued)

*Primary Examiner* — Sharon X Wen
*Assistant Examiner* — Peter Johansen
(74) *Attorney, Agent, or Firm* — Kilpatrick Townsend & Stockton LLP

(57) ABSTRACT

The invention provides a system that comprises pharmaceutical agents for use in immunotherapy for reducing the side-effects of an antigen-recognizing receptor against antigen-expressing non-target cells in an individual. The system includes an antigen-recognizing receptor that specifically recognizes an antigen on target cells and at least on one hematopoietic cell type in the individual. The antigen-recognizing receptor is exemplified by chimeric antigen receptors (CAR) be expressed on the surface of an immune effector cells. The system also includes hematopoietic cells resistant to recognition of the same antigen by the antigen-recognizing receptor.

11 Claims, 8 Drawing Sheets
Specification includes a Sequence Listing.

(56) References Cited

OTHER PUBLICATIONS

Porter et al., "Chimeric Antigen Receptor-Modified T Cells in Chronic Lymphoid Leukemia", The New England journal of Medicine, vol. 365, No. 8, Aug. 25, 2011, pp. 725-733.
Schendel et al., "Limitations for TCR gene therapy by MHC-restricted fratricide and TCR-mediated hematopoietic stem cell toxicity", Oncoimmunology, vol. 2, No. 1, Jan. 2013, 3 pages.
Taniguchi et al., "2B4 inhibits NK-cell fratricide", Blood, vol. 110, No. 6, Sep. 15, 2007, pp. 2020-2023.
Uchiyama et al., "Development of novel humanized anti-CD20 antibodies based on affinity constant and epitope", Cancer Science, vol. 101, No. 1, Jan. 1, 2010, pp. 201-209.
U.S. Appl. No. 14/952,448, First Action Interview Pilot Program Pre-Interview Communication dated Jan. 23, 2018, 3 pages.
CD33 [Uniport ID: P20138], Available online at: https://register.epo.org/application?number=EP15196309&Ing=en&tab=doclist, 3 pages.
Raji (ATCC® CCL86™), Available online at: http://www.lgcstandards-atcc.org/Products/All/CCL-86.aspx?geo, Accessed from Internet on: Nov. 18, 2019, 2 pages.
Vor Biopharma, Available online at: http://www.vorbiopharma.com, Accessed from Internet on: Nov. 18, 2019, 3 pages.
U.S. Appl. No. 14/952,448, Final Office Action dated Jun. 21, 2018, 8 pages.
U.S. Appl. No. 14/952,448, Notice of Allowability dated Dec. 28, 2018, 2 pages.
U.S. Appl. No. 14/952,448, Notice of Allowance dated Nov. 30, 2018, 8 pages.
Anaya et al., Autoimmunity: From Bench to Bedside, El Rosario University Press, Jul. 18, 2013, 70 pages.
Bailey et al., M.V. Gene Editing for Immune Cell Therapies, Nature Biotechnology, vol. 37, No. 12, Jun. 3, 2019, pp. 1425-1434.
Belicha-Villanueva et al., What Is the Role of Alternate Splicing in Antigen Presentation by Major Histocompatibility Complex Class I Molecules, Immunologic Research, vol. 46, No. 1-3, Mar. 2010, pp. 32-44.
Bergom et al., An Alternatively Spliced Isoform of Pecam-1 Is Expressed at High Levels in Human and Murine Tissues, and Suggests a Novel Role for the C-terminus of PECAM-1 in Cytoprotective Signalling, Journal of Cell Science, vol. 121, Pt. 8, Apr. 15, 2008, pp. 1235-1242.
Borot et al., Gene-edited Stem Cells Enable CC33-directed Immune Therapy for Myeloid Malignancies, Proceedings of the National Academy of Sciences USA, vol. 116, No. 24, Jun. 11, 2019, pp. 11978-11987.
Brentjens et al., CD19-Targeted T Cells Rapidly Induce Molecular Remissions in Adults with Chemotherapy-Refractory Acute Lymphoblastic Leukemia, Science Translational Medicine, vol. 5, No. 177, Mar. 20, 2013, pp. 1-19.
Bubien et al., Transfection of the CD20 Cell Surface Molecule Into Ectopic Cell Types Generates a Ca2+ Conductance Found Constitutively in B Lymphocytes, Journal of Cell Biology, vol. 121, No. 5, Jun. 1993, pp. 1121-1132.
Cong et al., Multiplex Genome Engineering Using CRISPR/Cas Systems, Science, vol. 339, No. 6121, Feb. 15, 2013, pp. 819-823.
Davila et al., Efficacy and Toxicity Management of 19-28z CAR T Cell Therapy in B Cell Acute Lymphoblastic Leukemia, Science Translational Medicine, vol. 6, No. 224, Feb. 19, 2014, pp. 1-23.
European Patent Application No. EP1519609.7, Response to the Opposition mailed on Nov. 18, 2019, 39 pages.
European Patent Application No. EP15196309.7, Response to First Summons mailed on Aug. 19, 2020, 16 pages.
European Patent Application No. EP15196309.7, Response to Opposition mailed on Aug. 21, 2020, 25 pages.
European Patent Application No. EP15196309.7, Response to Second Summons mailed on Jan. 19, 2021, 25 pages.
European Patent Application No. EP15196309.7, Hoffmann Eitle Response to Second Summons mailed on Jan. 19, 2021, 11 pages.
European Patent Application No. EP15196309.7, Summons to attend Oral Proceeding mailed on Mar. 6, 2020, 11 pages.
European Patent Application No. EP15196309.7, Summons to Attend Oral Proceedings mailed on Sep. 29, 2020, 8 pages.
European Patent Application No. EP16856410.2, European Search Report dated Apr. 25, 2019, 9 pages.
European Patent No. EP3025719, Notice of Opposition mailed on Jun. 26, 2019, 34 pages.
Epstein et al., Morphological and Virological Investigations on Cultured Burkitt Tumor Lymphoblasts (Strain Raji), Journal of the National Cancer Institute, vol. 37, No. 4, Oct. 1966, pp. 547-559.
Falkenburg et al., T Cell Therapy in Allogeneic Stem Cell Transplantation, Biology of Blood and Marrow Transplantation, vol. 14, 1 Supplement 1, Jan. 2008, pp. 136-141.
Gill et al., Preclinical Targeting of Human Acute Myeloid Leukemia and Myeloablation Using Chimeric Antigen Receptor-modified T Cells, Blood, vol. 123, No. 15, Apr. 10, 2014, pp. 2343-2354.
Gomes-Silva et al., CD7-Edited T Cells Expressing a CD7-specific CAR for the Therapy of T-cell Malignancies, Blood, vol. 130, No. 3, Jul. 20, 2017, pp. 285-296.
Grupp et al., Chimeric Antigen Receptor-Modified T Cells for Acute Lymphoid Leukemia, The New England Journal of Medicine, vol. 368, No. 16, Apr. 18, 2013, pp. 1509-1518.
Henig et al., Hematopoietic Stem Cell Transplantation—50 Years of Evolution and Future Perspectives, Rambam Maimonides Medical Journal, vol. 5, No. 4, Oct. 29, 2014, 15 pages.
Janeway et al., The Immune System in Health and Disease, Immunobiology, 1994, 5 pages.
Kebriaei et al., Infusing CD-19-directed T Cells to Augment Disease Control in Patients Undergoing Autologous Hematopoietic Stem-cell Transplantation for Advanced B-lymphoid Malignancies, Human Gene Therapy, vol. 23, No. 5, May 2012, pp. 444-450.
Kim et al., Genetic Inactivation of CD33 in Hematopoietic Stem Cells to Enable CART Cell Immunotherapy for Acute Myeloid Leukemia, Cell, vol. 173, No. 6, May 31, 2018, pp. 1439-1453.
Klein et al., Epitope Interactions of Monoclonal Antibodies Targeting CD20 and Their Relationship to Functional Properties, MAbs, vol. 5, No. 1, Jan.-Feb. 2013, pp. 22-33.
Kolb, Graft-versus-Leukemia Effects of Transplantation and Donor Lymphocytes, Blood, vol. 112, No. 12, Dec. 1, 2008, pp. 4371-4383.
Kuijpers et al., CD20 Deficiency in Humans Results in Impaired T Cell-independent Antibody Responses, Journal of Clinical Investigation, vol. 120, No. 1, Jan. 4, 2010, pp. 214-222.
Mali et al., RNA-Guided Human Genome Engineering Via Cas9, Science, vol. 339, No. 6121, Feb. 15, 2013, pp. 823-826.
Marelli-Berg et al., An Immunologist's Guide to CD31 Function in T-cells, Journal of Cell Science, vol. 126, Pt. 11, Jun. 1, 2013, pp. 2343-2352.
Porter et al., Chimeric Antigen Receptor-Modified T Cells in 038 Chronic Lymphoid Leukemia; N Engl J Med., Aug. 25, 2011, 365(8):725-733.
Roberts et al., CD45-deficient Severe Combined Immunodeficiency Caused by Uniparental Disomy, Proceedings of the National Academy of Sciences USA, vol. 109, No. 26, Jun. 26, 2012, pp. 10456-10461.
Shono et al., Bone Marrow Graft-versus-host Disease: Early Destruction of Hematopoietic Niche After MHC-mismatched Hematopoietic Stem Cell Transplantation, Blood, vol. 115, No. 26, Jul. 1, 2010, pp. 5401-5411.
Ukena et al., Human Regulatory T Cells in Allogeneic Stem Cell Transplantation, Blood, vol. 118, No. 13, Sep. 29, 2011, pp. e82-e92.
Zebedee et al., Comparison of Mouse Ly5 and Ly5b Leucocyte Common Antigen Alleles, Developmental Immunology, vol. 1, No. 4, Feb. 1991, pp. 243-254.
Zernich et al., Natural HLA Class I Polymorphism Controls the Pathway of Antigen Presentation and Susceptibility to Viral Evasion, Journal of Experimental Medicine, vol. 200, No. 1, Jul. 5, 2004, pp. 13-24.
EP 30125719 B1 opposition—Written submission in response to communication from Opposition Division: Miltenyi, dated Mar. 2, 2021.
EP 30125719 B1 opposition—Auxiliary requests accompanying written submission: Miltenyi, dated Mar. 2, 2021.

(56) References Cited

OTHER PUBLICATIONS

EP 30125719 B1 opposition—Response to patentee's submission of Jan 19, 2021: Opponent, dated Mar. 5, 2021.
EP 30125719 B1 opposition—Communication in advance of oral proceedings: Opponent, dated Mar. 5, 2021.
Document D44: URNOV, "Genome editing with engineered zinc finger nucleases" Nature Reviews Genetics, 2010, vol. 11 (9), p. 636-646.
Document D45: CHO et al., "Targeted genome engineering in human cells with the Cas9 RNA-guided endonuclease" Nature Biotechnology, 2013, vol. 31 (3), p. 230-232.
Document D46: KOO et al., "Measuring and Reducing Off-Target Activities of Programmable Nucleases Including CRISPR-Cas9" Mol Cells, 2015, vol. 38(6), 475-481.
Document D47: CRADICK et al., "Cradick et al., CRISPR/Cas9 systems targeting-globin and CCR5 genes have substantial off-target activity" Nucleic Acids Research, 2013, vol. 41 (20), p. 9584-9592.
EP 30125719 B1 opposition—Response to opponent's submission of Mar. 5, 2021: Miltenyi, dated Mar. 12, 2021.
Document D48: KIM E. et al. 2012, "Precision genome engineering with programmable DNA-nicking enzymes" Genome Res. 2002, vol. 22, p. 1327-1333.
Document D49: Clinical study listed on Clinicaltrials.gov website under Identifier NCT00842634: "Autologous T-cells genetically modified at the CCR5 gene by zink finger nucleases Sb-728 for HIV" (downloaded Dec. 3, 2020).
Document D50: TEBAS et al. 2014 "Gene Editing of CCR5 in Autologous CD4 T Cells of Persons" N Engl J Med. 2014; vol. 370(10): p. 901-910.
Document D51: MANGHWAR et at 2020 "CRISPR/Cas Systems in Genome Editing: Methodologies and Tools for sgRNA Design, Off-Target Evaluation, and Strategies to Mitigate Off-Target Effects" Adv. Sci. 2020, vol. 7: 1902312 (p. 1-16).
EP 30125719 B1 opposition—Supplementary response to the objection raised by the opponent: Miltenyi, dated Mar. 17, 2021.
Document 52: N. HOLMES. "CD45: All is not yet crystal clear" Immunology 2005, vol. 117, p. 145-155.
Protein (amino acid) sequence data for CD33, CD34, CD45, CD123, CD133, and CD19, From Swiss-Prot database dated Sep. 5 and Oct. 3, 2012.
EP 30125719 B1 opposition—Consolidated list of cited documents.
EP 30125719 B1 opposition—Results of oral proceedings dated Mar. 19, 2021.

FIG 5

Comparison of $Ly5^a$ and $Ly5^b$ Sequence Changes

| Nucleotide position[a] | | Nucleotide | | Amino-acid position | Residue | | Protein domain[b] |
|---|---|---|---|---|---|---|---|
| | | CD45.2 | CD45.1 | | CD45.2 | CD45.1 | |
| 943 | Exon 10 | A | G | 277 | K | E | Extracellular |
| 1238 | Exon 12 | T | C | 375 | V | A | Extracellular |
| 1251 | | G | T | 379 | E | D | Extracellular |
| 1252 | | T | C | 380 | S | P | Extracellular |
| 1461 | | G | A | 449 | — | | Extracellular |
| 1472 | Exon 14 | A | C | 453 | N | T | Extracellular |

FIG 8

Coding sequence variants identified in PTPRC (human CD45)

| Designation[1] | AA no.[2] | Codon pos.[3] | Base identity - Major | Base identity - Minor | Phenotype[4] | Freq.[5] |
|---|---|---|---|---|---|---|
| e4_A54G | 27 | 1 | A | G | Thr→Ala, splicing | ND |
| e4_C99A | 28 | 3 | C | A | His→Gln, splicing | ND |
| e4_C77G | 34 | 3 | C | G | Splicing | 0.011 |
| e4_C77T | 34 | 3 | C | T | Synonymous, splicing? | ND |
| e5_G69C | 98 | 1 | G | C | Asp→His | ND |
| e6_T127A | 164 | 2 | T | A | Ile→Asn | ND |
| e6_A138G | 168 | 1 | A | G | Thr→Ile | 0.015 |
|  |  |  |  |  | splicing | 0.237[6] |
| rs12129883 | 261 | 1 | A | C | Ile→Leu | 0.005 |
| rs2274367 | 304 | 1 | G | A | Glu→Lys | ND |
| rs4696162 | 398 | 2 | C | T | Thr→Ile | ND |
| rs12136658 | 545 | 3 | T | A | His→Gln | ND |
| rs6740378 | 747 | 3 | C | T | Synonymous | ND |
| rs1058191 | 1253 | 3 | T | C | Synonymous | 0.02 |
| rs2298872 | 1260 | 1 | A | C | Ser→Arg | 0.003 |

ND, insufficient data.
[1] Where a published name exists, this is used prefixed with the exon number, otherwise the dbSNP id no. is used.
[2] Amino acid numbered from the mature N terminus of CD45RABC.
[3] Position of variation within the amino acid codon.
[4] Known phenotypic effects; other effects probably exist.
[5] Allele frequency, where evidence in Caucasians, except for [6], varies between populations.
[6] In Japanese.

COMBINATION OF IMMUNE EFFECTOR CELLS SPECIFIC FOR A TARGET ANTIGEN AND HEMATOPOIETIC CELLS THAT EXPRESS THE TARGET ANTIGEN IN AN ALTERED FORM

REFERENCE TO RELATED APPLICATIONS

This application is a divisional application of U.S. application Ser. No. 14/952,448, filed Nov. 25, 2015 (pending) which claims the priority benefit of DE 102014224071.9, filed Nov. 26, 2014. The aforelisted priority applications are hereby incorporated herein by reference in their entirety for all purposes.

FIELD OF INVENTION

This present invention relates to the treatment of diseases such as cancer using antigen-recognizing receptors, e.g. chimeric antigen receptors (CARs) on immune effector cells in combination with the transfer of polymorphic or genetically modified hematopoietic cells to circumvent or reduce side-effects of said antigen-recognizing receptor.

BACKGROUND

Targeted immunotherapies are based on the recognition of antigens, defined structures on diseased cells or pathogens, by immune receptors that are either soluble or present on the surface of immune cells. Recognition and binding of the antigen by the immune receptor usually triggers effector functions that eventually lead to the destruction of the respective pathogen or cell. Soluble immune receptors include natural or synthetic antibodies, antibody derived molecules and other structures, which upon binding to an antigen trigger the complement system or recruit and in most cases activate effector cells. Direct triggering of cell effector function can be induced upon antigen recognition by cell membrane bound immune receptors such as T cell receptors (TCR) present on T lymphocytes. TCRs specifically recognize antigenic peptides that are presented on human leukocyte antigen (HLA) molecules on virus infected or malignant cells, which leads to activation and T cell mediated killing of target cells. Antigen-specific T cells of the in vivo occurring natural repertoire can be applied for therapeutic purposes using various methods. Alternatively antigen-targeting cells can be generated through the genetic insertion of engineered immune receptors, such as transgenic TCRs or CARs into T cells or other immune effector cells including natural killer (NK) cells. Commonly, CARs comprise a single chain fragment variable (scFv) of an antibody specific for a certain target antigen coupled via hinge and transmembrane regions to cytoplasmic domains of T-cell signaling molecules. The most common lymphocyte activation moieties include a T cell co-stimulatory (e.g. CD28, CD137, OX40, ICOS, and CD27) domain in tandem with a T cell triggering (e.g. CD3$\zeta$) moiety. The CAR-mediated adoptive immunotherapy allows CAR-grafted cells to directly recognize the desired antigen on target cells in a non-HLA-restricted manner.

Cancer is a broad group of diseases involving deregulated cell growth. In cancer, cells divide and grow uncontrollably, forming malignant tumors, and invading nearby parts of the body. The cancer may also spread to more distant parts of the body through the lymphatic system or bloodstream. There are over 200 different known cancers that affect humans. Whereas good treatment options are available for many cancer types, others still represent unmet medical needs. Cancers of the hematopoietic system can be roughly divided into different subtypes. Leukemias generally affect the primary lymphatic organs, which are the bone marrow as well as the thymus, and arise from hematopoietic progenitor populations. Lymphomas on the other hand are usually derived from mature lymphocytes and originate from secondary lymphatic organs. The current first line treatment for most hematopoietic cancers involves the administration of chemotherapeutic agents, radiation therapy or a combination of both. In many cases such therapies are combined with or followed by hematopoietic stem cell transfer (HSCT), where the graft versus leukemia (GVL) effect mediated by donor-derived lymphocytes, especially T cells, can lead to the eradication of cancer cells that survived pre-conditioning chemo- or radiotherapies and result in complete remission. Depending on the type of hematological malignancy, the patients' condition and the availability of hematopoietic stem cell grafts various versions of HSCT are regularly performed in the clinics. The desired GVL effect is only achieved in allogeneic HSCT, which at the same time is often accompanied by the occurrence of graft versus host disease (GvHD), a serious and sometimes fatal complication. Moreover, in all cases, persisting cancer stem cells often lead to disease relapse.

The CAR provides a promising approach for adoptive cell immunotherapy for cancer. CAR T cell therapy has been tested for the treatment of various cancers, hematopoietic cancers but also tumors derived from other tissues, in clinical or pre-clinical studies and CARS for multiple different target antigens have been evaluated (Anurathapan, U., Leen, A. M., Brenner, M. K., and Vera, J. F. (2014). Engineered T cells for cancer treatment. Cytotherapy 16, 713-733.). Amongst hematological cancers, CAR modified autologous T cells present a promising tool to improve the GVL effect without the complication of GvHD. As such CARs have been applied most successfully for the treatment of B-cell derived cancers such as ALL and CLL using CD19 as target antigen (Grupp, S. A., Kalos, M., Barrett, D., Aplenc, R., Porter, D. L., Rheingold, S. R., Teachey, D. T., Chew, A., Hauck, B., Wright, J. F., et al. (2013). Chimeric antigen receptor-modified T cells for acute lymphoid leukemia. The New England journal of medicine 368, 1509-1518. Porter, D. L., Levine, B. L., Kalos, M., Bagg, A., and June, C. H. (2011). Chimeric antigen receptor-modified T cells in chronic lymphoid leukemia. The New England journal of medicine 365, 725-733.). However, for various other cancers and target antigens so called on-target off-tumour side effects have been observed (Morgan, R. A., Yang, J. C., Kitano, M., Dudley, M. E., Laurencot, C. M., and Rosenberg, S. A. (2010). Case report of a serious adverse event following the administration of T cells transduced with a chimeric antigen receptor recognizing ERBB2. Molecular therapy 18, 843-851.). In these cases the CAR T cells specifically targeted the desired antigen but the target antigen expression was not restricted to the cancer. Consequently healthy tissues were damaged, which in some cases led to serious side effects or even death. Therefore the application of CAR T cell therapy to a wider range of cancers has been hampered by the lack of suitable target antigens.

Antigen specific T cells can be used in combination with HSCT. In multiple clinical trials patients with lymphoid leukemias were treated with CAR T cells specific for CD19 in order to achieve a temporary remission and bridge the time until the identification of a suitable donor for HSCT (Brentjens, R. J., Davila, M. L., Riviere, I., Park, J., Wang, X., Cowell, L. G., Bartido, S., Stefanski, J., Taylor, C., Olszewska, M., et al. (2013). CD19-targeted T cells rapidly induce molecular remissions in adults with chemotherapy-refractory acute lymphoblastic leukemia. Science translational medicine 5, 177ra138.). A similar approach has been proposed for a CAR directed to CD123, an antigen that is expressed by myeloid leukemias, but also present on the healthy myeloid cell compartment (Gill, S., Tasian, S. K., Ruella, M., Shestova, O, Li, Y., Porter, D. L., Carroll, M., Danet-Desnoyers, G., Scholler, J., Grupp, S. A., et al. (2014). Preclinical targeting of human acute myeloid leukemia and myeloablation using chimeric antigen receptor-modified T cells. Blood 123, 2343-2354.). The myeloid depletion efficiency has been shown for a CD123 CAR in a pre-clinical model suggesting that CD123 CAR T cells could be used as part of a pre-conditioning regiment before HSCT. However, in order to avoid on-target off-tumour toxicity CAR T cells have to be completely absent at the time of HSCT as well as thereafter. For the CD19 CAR approach the application of CAR T cells and the HSCT might be month apart and some CD19 CAR T cells have been shown to have limited life spans (Brentjens, R. J., Davila, M. L., Riviere, I., Park, J., Wang, X., Cowell, L. G., Bartido, S., Stefanski, J., Taylor, C., Olszewska, M., et al. (2013). CD19-targeted T cells rapidly induce molecular remissions in adults with chemotherapy-refractory acute lymphoblastic leukemia. Science translational medicine 5, 177ra138.). For the CD123 CAR, however, CAR T cell treatment has to be followed by HSCT within days to avoid potential myelocytopenia and rapid CAR T cell depletion presents a significant challenge.

For engineered T cells expressing a CAR or a transgenic TCR on-target off-tumor side effects can also include the so called T cell fratricide, if the target antigen is expressed by the T cells themselves. For a CD38 CAR T cell fratricide observed during in vitro culture could be prevented using an anti-CD38 antibody that blocked the CAR-target interaction. Such approach, however, has to date not been tested in vivo. Antibody mediated blocking of fratricide in vivo has only been shown for NK cells in a murine model using a monoclonal antibody against CD244 (Taniguchi, R. T., Guzior, D., and Kumar, V. (2007). 2B4 inhibits NK-cell fratricide. Blood 110, 2020-2023.).

In a clinical safety study using a CAIX CAR for the treatment of renal cell carcinoma on-target off-tumor toxicity was reported due to low target antigen expression in the liver (Lamers, C. H., Sleijfer, S., van Steenbergen, S., van Elzakker, P., van Krimpen, B., Groot, C., Vulto, A., den Bakker, M., Oosterwijk, E., Debets, R., et al. (2013). Treatment of metastatic renal cell carcinoma with CAIX CAR-engineered T cells: clinical evaluation and management of on-target toxicity. Molecular therapy 21, 904-912.). On-target off-tumor toxicity could be prevented by treatment with a CAIX monoclonal antibody, which blocked the CAR-target interaction. However, with antibody treatment the anti-tumor response was equally undetectable.

For T cells expressing a transgenic TCR, fratricide can potentially be circumvented, if an allogeneic T cell donor negative for the targeted HLA-type is used (Leisegang, M., Wilde, S., Spranger, S., Milosevic, S., Frankenberger, B., Uckert, W., and Schendel, D. J. (2010). MHC-restricted fratricide of human lymphocytes expressing survivin-specific transgenic T cell receptors. The Journal of clinical investigation 120, 3869-3877. Schendel, D. J., and Frankenberger, B. (2013). Limitations for TCR gene therapy by MHC-restricted fratricide and TCR-mediated hematopoietic stem cell toxicity. Oncoimmunology 2, e22410).

Genetic modification of HLA molecules in order to create cells that are no longer the target of particular transgenic or naturally occurring TCRs is disclosed in WO2012012667A2. Designer nucleases such as ZFNs or TALENs are applied for the deletion of one or more HLA molecules.

Designer nuclease mediated modification of hematopoietic cells including T cells and hematopoietic stem cells (HSC) has been described for the generation of HIV resistant T cells (Holt, N., Wang, J., Kim, K., Friedman, G., Wang, X., Taupin, V., Crooks, G. M., Kohn, D. B., Gregory, P. D., Holmes, M. C., et al. (2010). Human hematopoietic stem/progenitor cells modified by zinc-finger nucleases targeted to CCR5 control HIV-1 in vivo. Nature biotechnology 28, 839-847.) (US20120309091A1). CCR5, a co-receptor required for HIV entry into T cells, is deleted using a ZFN. Generated CCR5 deleted T cells have been shown to be insensitive to HIV infection.

The development of designer nucleases (ZFN, TALEN and CRISPR/Cas) as well as transcriptional repressors (zinc finger, TALE- or CRISPR/Cas-based fusion proteins) for the deletion or transcriptional repression of the hematopoietic surface proteins CTLA-4 and PD-1, optionally in combination with CARs or transgenic TCRs, has been disclosed in WO2014059173A2.

Taken together, in recent years there has been strong progress in the development of targeted immunotherapies for multiple diseases including some types of cancer. However, the lack of suitable target molecules for therapies with antigen-recognizing receptors and in particular CAR T cells has been a major obstacle. Therefore, there is a need for the development of novel therapies for the treatment of diseases, such as cancer, that enable the utilization of alternative target molecules, and reduce or avoid the side-effects often associated with current targeted immunotherapies in general, and CAR T cell therapies in particular.

SUMMARY OF THE INVENTION

Surprisingly, it was found that the side-effects of an antigen-recognizing receptor, which recognizes an antigen present on target cells, but also on at least one hematopoietic cell type, can be reduced by application of hematopoietic cells resistant to recognition by said antigen recognizing receptor in a combination immunotherapy. Therefore this invention relates to a combination immunotherapy for disease in an individual, including but not restricted to cancer, comprising i) an antigen-recognizing receptor, which recognizes an antigen present on target cells, but also on at least one hematopoietic cell type of said individual, and ii) hematopoietic cells resistant to recognition of said antigen by said antigen-recognizing receptor.

As an effect of the present invention a reduction of side-effects of antigen-recognizing receptors by application of hematopoietic cells resistant to recognition by said antigen-recognizing receptor in a combination therapy can be observed. Furthermore the invention relates to a method or system that allows the utilization of a group of antigens as potential targets for immunotherapy, that are present on at least one hematopoietic cell type, and therefore are not suitable targets for immunotherapies currently known in the art. In one embodiment said hematopoietic cells resistant to recognition of said antigen-recognizing receptor express a naturally occurring version of said antigen. In another embodiment said hematopoietic cells resistant to recognition of said antigen-recognizing receptor are genetically modified to express an altered version of said antigen.

BRIEF DESCRIPTION OF THE DRAWINGS

FIG. 5: Table from the manuscript of Zebedee, S. L.; Barritt, D. S.; and Raschke, W. C. (1991. Comparison of Mouse Ly5a and Ly5b Leucocyte Common Antigen Alleles. Developmental Immunology, 1, 243-254) showing the comparison of sequence change between Ly5a and Ly5b which is mouse CD45.1 and CD45.2 isoforms. Thanks to the existence of 2 separate antibodies (anti-CD45.2 and anti-CD45.1), both isoforms can be detected and discriminated.

FIG. 8: represents Table 1 from the manuscript of Holmes (Immunology (2006), vol. 117: 145-155) which details the known (functional) isoforms of human CD45.

DETAILED DESCRIPTION OF THE INVENTION

Figure 1:
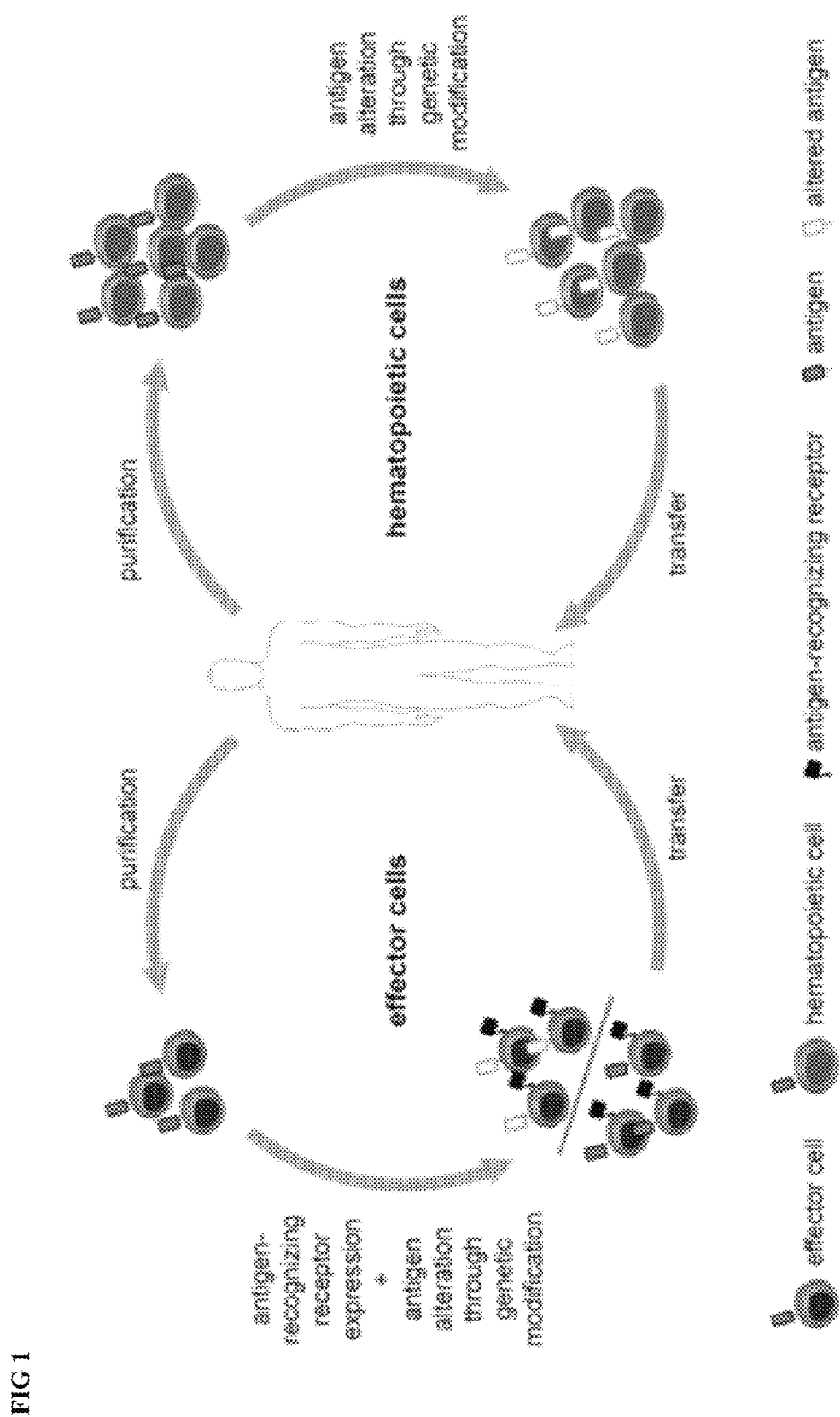
FIG. 1: Schematic representation of a preferred embodiment of the invention, detailing the application of immune effector cells expressing an antigen-recognizing receptor and hematopoietic cells resistant to recognition of said antigen by said antigen recognizing receptor to an individual.
Figure 2:
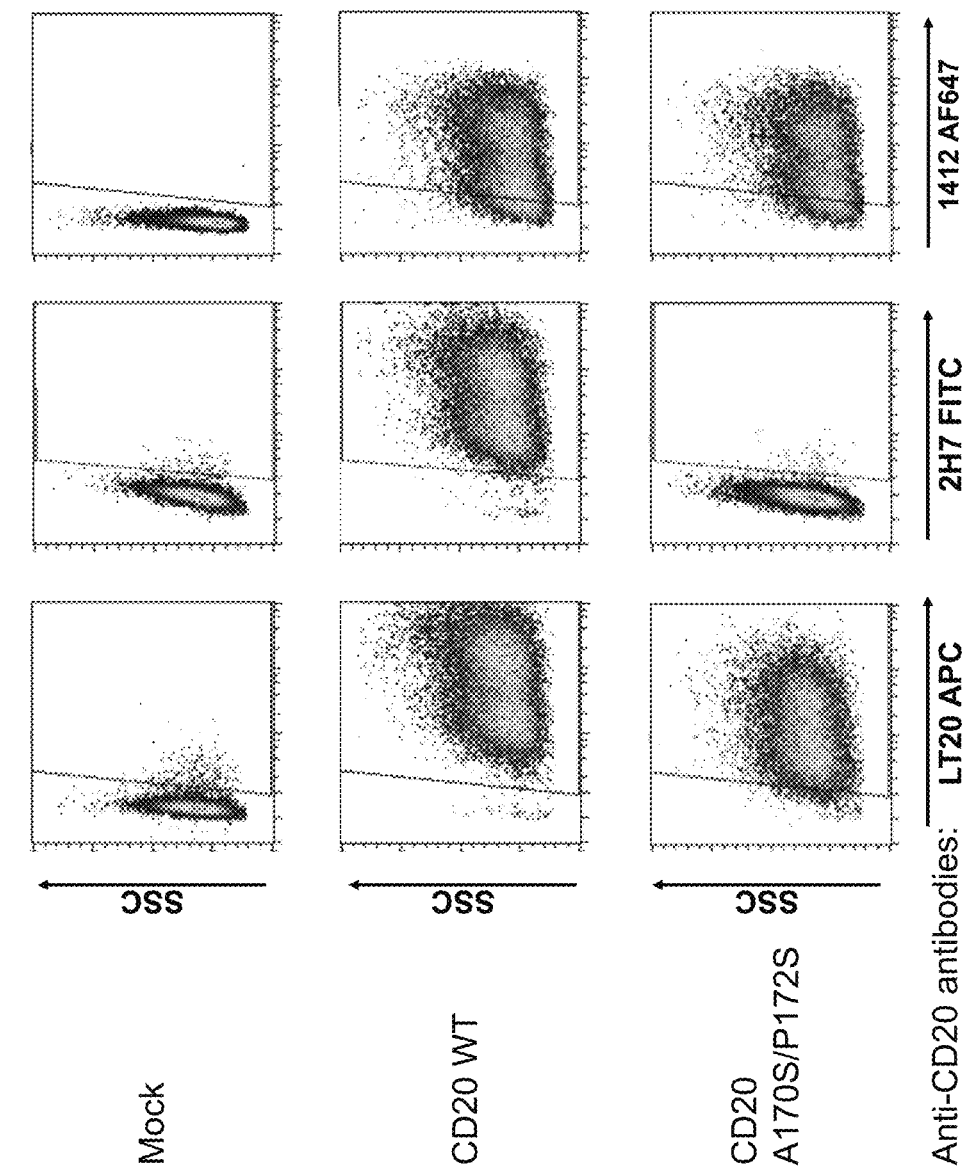
FIG. 2: Expression of human CD20 WT (SEQ ID NO:3) and CD20 mutant A170S/P172S. HEK 293T cells were either mock transfected or transfected using the pMACS LNGFR-IRES plasmid (Miltenyi Biotec GmbH) encoding either wild type CD20 (annotated CD20 WT) or a mutated CD20 (CD20 A170S/P172S). Two days after transfection, the HEK 2913T cells were analysed by Flow cytometry for detection of the CD20 antigen using different anti-CD20 antibodies (staining of CD20 extracellular epitopes with clone LT20 and clone 2H7 and intracellular staining of CD20 C-terminal epitope with clone 1412).
Figure 3:
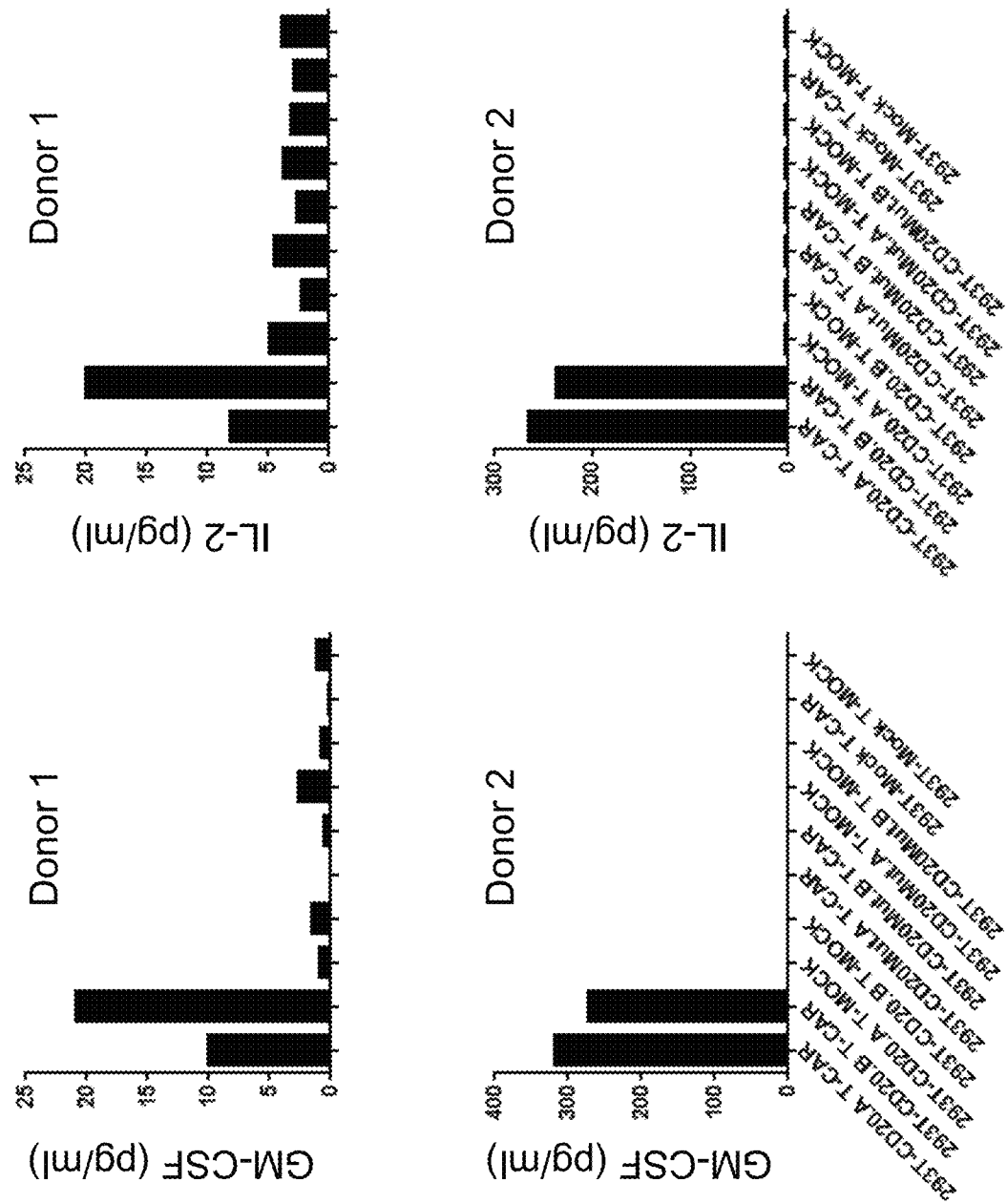
FIG. 3: Cytokine expression of human T cells modified to express an antigen-recognizing receptor directed against the CD20 antigen (annotated T-CAR) or human T cells not engineered to express an antigen-recognizing receptor (annotated T-MOCK) co-cultured with HEK 293 T cells encoding either wild type CD20 (annotated 293T-CD20) or a mutated CD20 A170S/P172S (annotated 293T-CD20Mut) or no antigen (annotated 293T-Mock). Results for the expression of either GM-CSF (left graphs) or IL-2 (right graphs) for T cells derived from 2 blood donors are represented. Cytokines were measured from the supernatant after 24 hour co-culture using the MACSPlex Cytokine kit of Miltenyi Biotec. X-axis represents the different conditions. A and B indicate experimental duplicates.
Figure 4:
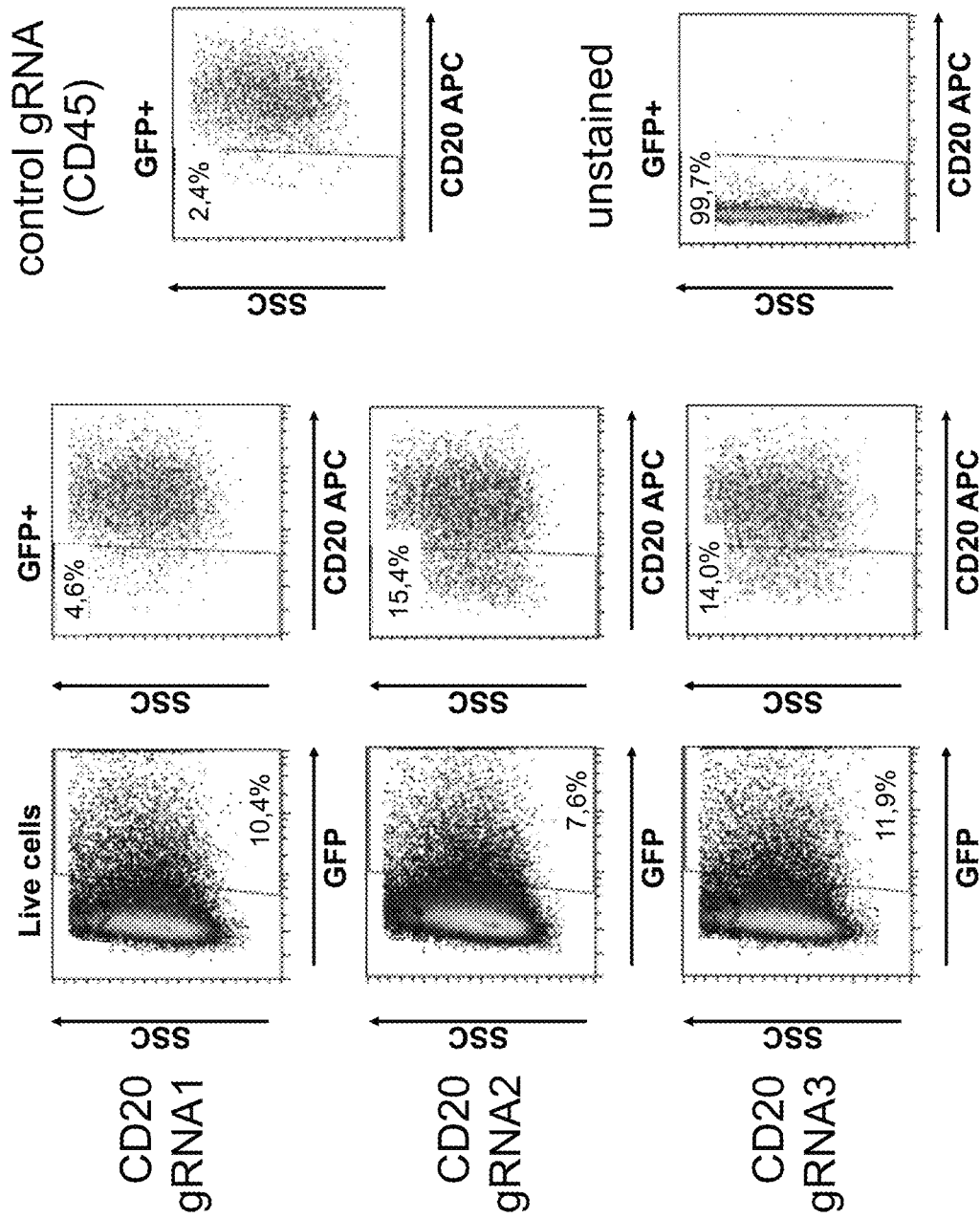
FIG. 4: Gene editing of the CD20 antigen using designer nucleases in order to abrogate recognition of the antigen by the antigen recognizing anti-CD20 antibody. The B cell lymphoma cell line Raji, naturally expressing CD20, was transfected by co-electroporation with 3 plasmids; one encoding the green fluorescent protein (as transfection control), one encoding the guide RNA sequences (gRNA 1-3) (see SEQ ID NO:4 and SEQ ID NO:5, SEQ ID NO:6 and SEQ ID NO:7, SEQ ID NO:8 and SEQ ID NO:9, respectively) and one encoding the nuclease Cas9. 5 days after gene-editing, the CD20 expression of the GFP positive Raji cells was analyzed by flow cytometry using the anti-CD20 antibody used to generate the CAR. The 2 dot plots on the right represent controls as indicated.
Figure 6:
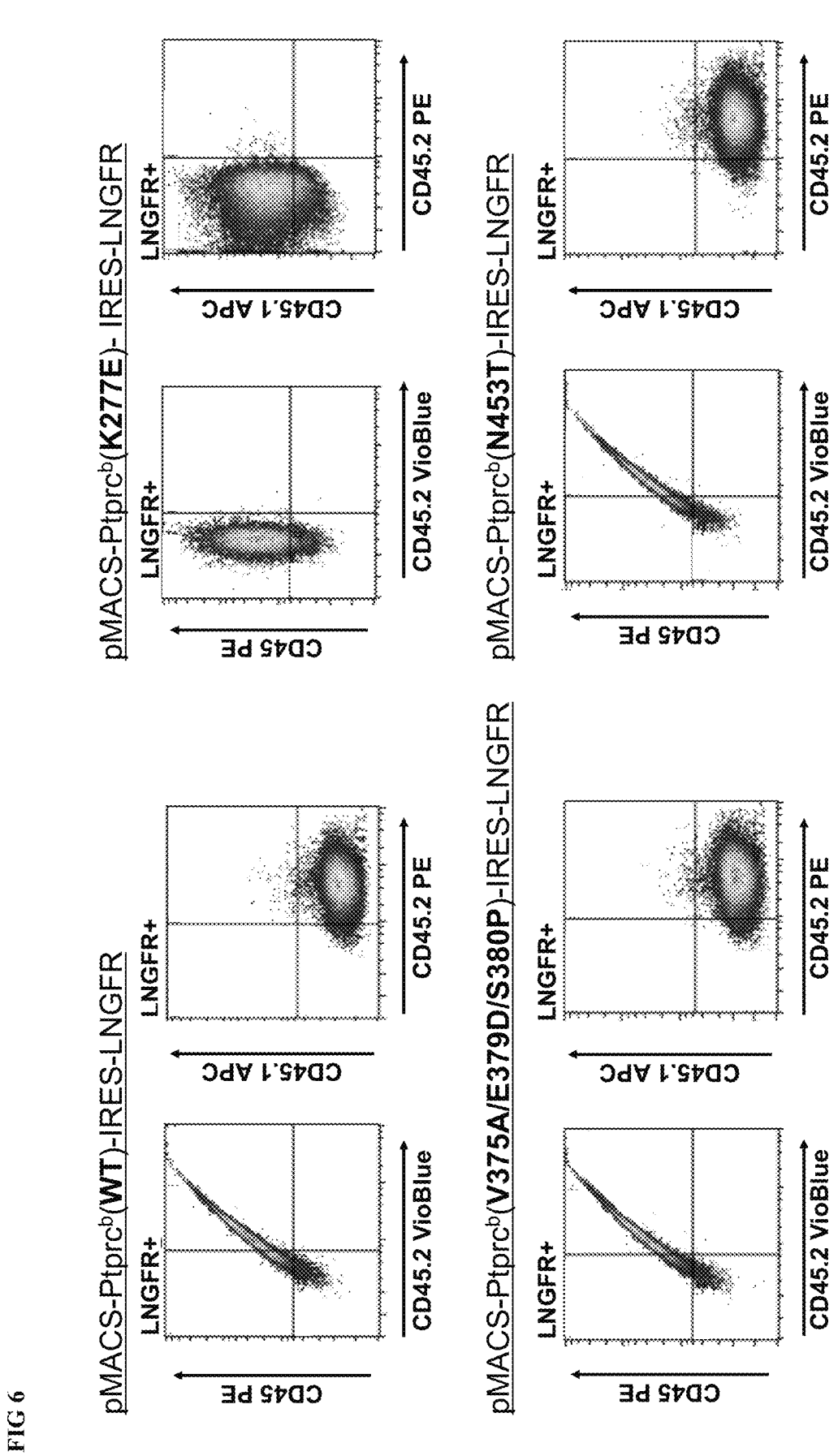
FIG. 6: Flow cytometry analysis of HEK 293 T cells transfected with the pMACS plasmid encoding either the WT Ptprcb (=CD45.2) or 3 different mutant versions (with the indicated mutations). An anti-CD45 antibody (recognizing both CD45.2 and CD45.1 isoforms) is used to confirm expression of the antigen. The WT sequence is CD45.2 positive and CD45.1 negative. Only the mutation of the amino acid K in position 277 to E allows the anti-CD45.1 antibody to bind the antigen and abrogates the binding of anti-CD45.2 antibody. The other mutations maintain the specificity for the anti-CD45.2 antibody.

In targeted therapies including those utilizing antigen recognizing receptors side-effects resulting from the presence of the target antigen on non-target cells represent a major hurdle for the treatment of diseases such as cancer. Such side-effects often include and sometimes are restricted to hematopoietic cells, which leads to the depletion of one or more hematopoietic subpopulations. The invention is based on the fact that small subsets of hematopoietic cells or the entire hematopoietic system can be replaced through transplantation. If applied hematopoietic cells are resistant to recognition of said antigen-recognizing receptor, they can be used to replace said depleted hematopoietic cells and present a way for treatment of the side-effects of an antigen recognizing receptor. Exemplarily, the concept of the present invention is shown by using antigens CD20 and CD45 and selected antigens thereof. But it is self-explanatory that the concept of the present invention is not restricted to these antigens, the selected variants thereof, and the cells used herein.

In one aspect the invention provides a system for use in immunotherapy for reducing the side-effects of an antigen-recognizing receptor against antigen-expressing non-target cells in an individual, comprising
  a) Said antigen-recognizing receptor wherein said antigen-recognizing receptor specifically recognizes an antigen on target cells in said individual;
  b) Hematopoietic cells resistant to recognition of said antigen by said antigen-recognizing receptor;
wherein said antigen is expressed on target cells in said individual and at least on one hematopoietic cell type of said individual.

In another aspect the invention provides the use of a system for use in immunotherapy for reducing the side-effects of an antigen-recognizing receptor against antigen-expressing non-target cells in an individual, the system comprising
  a) Said antigen-recognizing receptor wherein said antigen-recognizing receptor specifically recognizes an antigen on target cells in said individual;
  b) Hematopoietic cells resistant to recognition of said antigen by said antigen-recognizing receptor;
wherein said antigen is expressed on target cells in said individual and at least on one hematopoietic cell type of said individual.

In a further aspect the invention provides a method for reducing the side-effects in an immunotherapy of an antigen-recognizing receptor against antigen-expressing non-target cells in an individual, comprising
  a) Application of the antigen-recognizing receptor to said individual, wherein said antigen recognizing receptor specifically recognizes an antigen on target cells in said individual;
  b) Application of hematopoietic cells resistant to recognition of said antigen by said antigen-recognizing receptor;
wherein said antigen is expressed on target cells in said individual and at least on one hematopoietic cell type of said individual.

In a further aspect the invention provides a method for producing a system for use in immunotherapy for reducing side-effects of an antigen-recognizing receptor against antigen-expressing non-target cells in an individual, wherein said system comprises two compositions, the method comprises
  a) generating an antigen-recognizing receptor wherein said antigen-recognizing receptor specifically recognizes an antigen on target cells in said individual, thereby generating the first composition of said system; and
  b) generating hematopoietic cells resistant to recognition of said antigen by said antigen-recognizing receptor, thereby generating the second composition of said system;
wherein said antigen is expressed on target cells in said individual and at least on one hematopoietic cell type of said individual.

The antigen-recognizing receptor may be a soluble receptor or may be expressed on the cell membrane of an immune effector cell. Cell membrane standing receptors include but are not restricted to natural receptors such as T cell receptors (TCR) or genetically engineered receptors such as transgenic TCRs or chimeric antigen receptors (CAR). Immune effector cells include but are not restricted to cells with cytotoxic effector function such as natural killer (NK) cells or T cells. Immune effector cells may comprise one or more cellular subsets. In a preferred variant of the invention the immune effector cell is a T cell engineered to express a CAR.

Said hematopoietic cells may be hematopoietic stem cells or hematopoietic progenitor cells.

Said hematopoietic cells resistant to recognition of said antigen by said antigen-recognizing receptor may have a deviation in said antigen, thereby altering the epitope recognized by said antigen-recognizing receptor resulting in a non-recognition or alleviated recognition by said antigen-recognizing receptor.

Said immune effector cells expressing said antigen-recognizing receptor may be said hematopoietic cells resistant to recognition of said antigen by said antigen-recognizing receptor, thereby avoiding fratricide.

Said immune effector cells expressing said antigen-recognizing receptor may be autologous or allogeneic transplants.

Said hematopoietic cells resistant to recognition of said antigen by said antigen-recognizing receptor may be autologous or allogeneic transplants.

Said antigen may be selected from, but not restricted to the group consisting of CD11a, CD18, CD19, CD20, CD31, CD34, CD44, CD45, CD47, CD51, CD58, CD59, CD63, CD97, CD99, CD100, CD102, CD123, CD127, CD133, CD135, CD157, CD172b, CD217, CD300a, CD305, CD317 and CD321.

Said antigen-recognizing receptor may comprise an antigen binding domain specifically recognizing the antigen CD20, and wherein said hematopoietic cells resistant to recognition of said antigen by said antigen-recognizing receptor may have a deviation in said antigen, thereby altering the epitope recognized by said antigen-recognizing receptor.

Said antigen-recognizing receptor may be a CAR, and wherein said antigen binding domain of said CAR may comprise the amino acid sequences SEQ ID NO:1 ($V_H$) and SEQ ID NO:2 ($V_L$). Said deviation in said CD20 antigen of said hematopoietic cells may be the amino acid substitution alanine to serine at position 170 and/or proline to serine at position 172 of said antigen CD20. The amino acid sequence of CD20 is given in SEQ ID NO:3.

The CAR may comprise, from the N-terminus to the C-terminus the extracellular part comprising at least one antigen binding domain, the transmembrane domain, and the at least one intracellular signaling domain. But the CAR may also comprise two or more members of polypeptides which together work as functional active CAR (e.g. switch-on CAR, conditionally active CAR, regulatable CAR, controllable CAR, multi chain CAR), e.g. a first polypeptide comprising at least one antigen binding domain, a first member of a dimerization pair, and a transmembrane domain; and a second polypeptide comprising a second member of a dimerization pair, and at least one intracellular signaling domain (for the key signaling of the active CAR), and optionally a transmembrane domain, wherein the CAR is activated upon dimerization by a dimerizer recognizing the members of the dimerization pair. Such CAR constructs with split key signaling and recognition modules are disclosed e.g. in WO2014/127261A1, WO2015017214A1, WO2015090229A1, WO2015142661A1, and WO2015150771A1. Engineered immune cells, preferentially T cells of the invention express a CAR of the invention, which is able to redirect antigen recognition based on the antigen binding specificity of the CAR.

The antigen-recognizing receptor of the invention such as a CAR recognizes and binds to the antigen via a certain epitope that composes only a small fraction of the antigen such as a peptide sequence of a protein. In turn, deviations in the epitope result in alteration of the binding affinity of the antigen-recognizing receptor to its antigen and may lead to the complete loss of specific binding. The invention exploits the effect that hematopoietic cells expressing a target antigen with such altered epitope are resistant to recognition and binding of the antigen-recognizing receptor of the invention. Such hematopoietic cells may be derived from an individual carrying a naturally occurring polymorphism that leads to the altered epitope or the altered epitope may be generated through genetic modification of said hematopoietic cells.

EMBODIMENTS

In one embodiment of the invention the antigen-recognizing receptor in the present method or system for reducing side-effects of an antigen-recognizing receptor against antigen-expressing non target cells is a CAR, which is expressed on an immune effector cell, preferentially on a T cell. Methods for purification and generating immune effector cells engineered to express a CAR are well known in the art. Immune effector cells, preferentially T cells can be obtained from a variety of sources including but not restricted to peripheral blood mononuclear cells (PBMCs), leukapheresis or bone marrow samples. For enrichment of these cells methods well known in the art can be used such as centrifugation through a Ficoll™ or PERCOLL™ gradient or positive/negative selection techniques such as fluorescent sorting (e.g. FACS) or magnetic sorting (e.g. MACS®). In one embodiment T cells obtained from an individual are magnetically labelled, for example with a magnetic bead coupled to antibodies specific for CD4 and for CD8, respectively, magnetically enriched and collected. In one embodiment the T cells engineered to express a CAR can be activated and expanded prior or after genetic engineering to increase the amount of engineered T cells generally using methods well known in the art, for example using polyclonal stimulation with anti-CD3/anti-CD28 beads or anti-CD3/anti-CD28 nanomatrices (EP2711418A1). Preferentially, said amount of engineered T cells is increased to a therapeutic effective amount.

In one embodiment of the invention an immune effector cell, preferentially a T cell expressing a CAR is generated using methods commonly known in the art. In a preferred embodiment T cells are engineered to express a CAR using a viral-based system for example a lentiviral vector or a γ-retroviral vector in order to achieve expression of the CAR in said T cells over several weeks, months or up to several years.

In one embodiment of the invention the CAR of the present method or system may be specific for the transmembrane protein CD20 that is expressed on diseased cells in an individual, for example a cancer cell such as a CD20 positive melanoma cell or a CD20 positive malignant hematopoietic cell for example a lymphoma cell or a chronic lymphoid leukemia cell or an acute lymphoid leukemia cell.

In one embodiment of the invention the hematopoietic cells resistant to recognition of said antigen by said CAR of the present method or system may be hematopoietic stem cells. These cells are altered in respect to said antigen for example CD20, so that the altered antigen is not recognized by said CAR. The deviation of said antigen may be a natural polymorphism of said antigen. In one embodiment of the invention said antigen in said hematopoietic cells, for example hematopoietic stem cells is altered through genetic modification of the genomic DNA of said hematopoietic cell. The genetic modification may involve the alteration of the genomic DNA sequence encoding said antigen recognized by said CAR.

Genetic modification of genomic DNA of cells such as hematopoietic cells, for example hematopoietic stem cells can be performed via methods well known in the art. The genetic modification may be performed by introduction of designer nucleases such as ZFN, TALEN or CRISPR/Cas into hematopoietic cells. Designer nucleases can be used to introduce strand breaks at specific locations of the genomic DNA of a cell, which may induce error prone repair mechanisms such as non-homologous end joining in the cell that lead to insertions or deletions at said location of the genomic DNA. Said location may be part of the genomic sequence encoding for said antigen and leads to absence of said antigen on said cells. In one embodiment of the invention a designer nuclease specific for said antigen, for example CD20 is applied to hematopoietic cells such as hematopoietic stem cells in order to generate a cell that lacks CD20 expression. The designer nuclease may be applied together with a template DNA in order to exploit the cellular repair mechanism of homologous recombination, that leads to inclusion of the genomic sequence of the template DNA at the site of the strand break introduced by the designer nuclease. In one embodiment of the invention a designer nuclease specific for the genomic sequence of CD20 is applied to hematopoietic cells such as hematopoietic stem cells, together with a template DNA that is largely homologous to the CD20 genomic sequence but contains one or more sequence alterations.

Both the immune effector cells engineered to express said CAR and the hematopoietic cells with said altered antigen are applied to an individual suffering from a disease associated with said antigen. In a preferred embodiment of the invention T cells engineered to express a CAR specific for CD20, and hematopoietic stem cells that express an altered version of CD20 not recognized by the CAR, are applied to an individual suffering from a disease associated with CD20. In one embodiment of the invention said disease is cancer including but not restricted to melanoma, lymphoma, chronic lymphoid leukemia or acute lymphoid leukemia. In one embodiment of the invention the individual may be depleted from hematopoietic cells including hematopoietic stem cells by a procedure commonly known in the art such as chemotherapy or radiation therapy. In one embodiment of the invention the application of T cells engineered to express a CAR and hematopoietic cells resistant to recognition of said antigen by said CAR is combined with additional treatments. Such treatments may include but are not restricted to the application of cytokines or inhibitors of cytokine signaling such as etanercept and tocilizumab.

In a preferred embodiment of the invention immune effector cells engineered to express said CAR, as well as hematopoietic cells with said altered antigen are derived from said individual suffering from a disease associated with said antigen before treatment. Such procedure is known in the art as an autologous cellular therapy. In another embodiment of the invention immune effector cells engineered to express said CAR as well as hematopoietic cells with said altered antigen are derived from one healthy individual and applied to another individual suffering from a disease associated with said antigen. Such procedure is known in the art as an allogeneic cellular therapy. The performance of the invention in a allogeneic setting may allow the targeting of an antigen with a naturally occurring polymorphism. In one embodiment of the invention hematopoietic cells, such as hematopoietic stem cells are derived from an individual with a naturally occurring polymorphism in the antigen associated with disease. In another embodiment of the invention hematopoietic cells, such as hematopoietic stem cells as well as immune effector cells, such as T cells are derived from an individual with a naturally occurring polymorphism in the antigen associated with disease. In one embodiment of the invention the natural TCR is depleted from such allogeneic T cells using methods commonly known in the art. In one embodiment of the invention allogeneic immune effector cells may be combined with autologous hematopoietic cells or autologous immune effector cells may be combined with allogeneic hematopoietic cells.

The antigen associated with disease may be present on the diseased cells and otherwise restricted to the immune effector cells engineered, such as T cells expressing an antigen-recognizing receptor, such as a CAR. In that case the side-effects of the antigen recognizing receptor will be restricted to the immune effector cells engineered to express the antigen recognizing receptor. Such side-effect is also known in the art as fratricide. Therefore, in one embodiment of the invention hematopoietic cells resistant to recognition of said antigen by said antigen recognizing receptors are said immune effector cells. Such immune effector cells may be engineered to express an antigen-recognizing receptor in addition to being genetically modified to express an altered version of said antigen. In another embodiment of the invention such immune effector cells may be resistant to fratricide due to the expression of a naturally occurring polymorphic version of said antigen.

Peptides derived from membrane associated, intra-as well as extracellular proteins are presented on the cells surface in complex with HLA molecules and can be specifically detected by TCRs. Specific HLA-antigen complexes can also be detected through transgenic TCRs. In one embodiment the invention provides a method for reducing the side effects of an immune effector cell, such as a T cell engineered to express a transgenic TCR, by application of hematopoietic cells that present an HLA-antigen complex, that cannot be recognized by said transgenic TCR. In one embodiment of the invention said HLA-antigen complex is formed by said HLA molecule with a peptide comprising an altered sequence, or said HLA-antigen complex is not formed, for example due to an altered peptide sequence. The alteration of the peptide sequence may be a natural polymorphism of said peptide or may be generated through genetic modification. Natural polymorphisms of peptides presented on HLA molecules are also known as minor antigens in the art.

The antigen used in the present method or system has to be expressed on target cells in the diseased individual and at least on one hematopoietic cell type. Preferentially, the said antigen is a cell surface antigen selected from, but not restricted to the group consisting of CD11a, CD18, CD19, CD20, CD31, CD34, CD44, CD45, CD47, CD51, CD58, CD59, CD63, CD97, CD99, CD100, CD102, CD123, CD127, CD133, CD135, CD157, CD172b, CD217, CD300a, CD305, CD317 and CD321. More preferentially, said antigen is CD20. In one embodiment of the invention said antigen has at least one a splice variant within the extracellular domain of said antigen suitable for generating different epitopes for antigen binding domains. In another embodiment of the invention said antigen has at least a natural polymorphic form within the extracellular domain of said antigen suitable for generating different epitopes for antigen binding domains. In another embodiment of the invention said antigen can be modified to a non-natural polymorphic form within the extracellular domain of said antigen suitable for generating different epitopes for antigen binding domains, wherein said non-natural polymorphic form does not alter or affect the natural function of hematopoietic cells in an individual. In another embodiment of the invention said antigen can be deleted without alteration or affecting the natural function of hematopoietic cells in said individual.

The antigen-recognizing receptor of the present invention (either in soluble form or as part of an immune cells) may be administered either alone, or as a pharmaceutical composition in combination with diluents and/or with other components such as IL-2 or other cytokines or cell populations. Briefly, pharmaceutical compositions of the present invention may comprise the antigen-recognizing receptor of the present invention as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives.

Preferentially, the compositions of the present invention are formulated for intravenous administration. The administration of cell compositions to the subject may be carried out in any convenient manner known in the art.

Pharmaceutical compositions of the present invention may be administered in a manner appropriate to the disease treated. Appropriate dosages may be determined by clinical trials. The quantity and frequency of administration will also be determined and influenced by factors such as the condition of the patient, and the type and severity of the patient's disease.

A pharmaceutical composition comprising immune cells as disclosed herein may be administered at a dosage of $10^2$ to $10^9$ cells/kg body weight, preferably $10^3$ to $10^6$ cells/kg body weight. The cell compositions may also be administered several times at these dosages. The compositions of cells may be injected directly into a tumor, lymph node, or site of infection. The cells may be activated and expanded to therapeutic effective amounts using methods known in the art. The cells of the invention may be used in combination with e.g. chemotherapy, radiation, immunosuppressive agents, antibodies or antibody therapies.

The hematopoietic cells resistant to recognition of said antigen by said antigen-recognizing receptor may be administered at the same time or at a time point prior to or after the antigen recognizing receptor of the invention or the immune effector cells expressing the antigen recognizing receptor of the invention, including CAR T cells. In a preferred embodiment hematopoietic cells resistant to recognition of said antigen by said antigen-recognizing receptor are administered before treatment with immune effector cells expressing the antigen recognizing receptor of the invention. Thereby partial or complete reconstitution of the blood system with hematopoietic cells resistant to recognition of said antigen by said antigen-recognizing receptor is achieved. For enhanced reconstitution chemotherapy treatment may be used prior to administration of said hematopoietic cells. In this setting during treatment with the immune effector cells the treated individual will always have an at least partially functional blood system, the complete depletion of the blood system will be avoided.

Definitions

Unless defined otherwise, technical and scientific terms used herein have the same meaning as commonly understood by one of ordinary skill in the art to which this invention belongs.

The term "diseased cell" as used herein refers to the state of a cell, tissue or organism that diverges from the normal or healthy state and may result from the influence of a pathogen, a toxic substance, irradiation or cell internal deregulation. "Diseased cell" may also refer to a cell that has been infected with a pathogenic virus. Further the term "diseased cell" may refer to a malignant cell or neoplastic cell that may constitute or give rise to cancer in an individual.

The term "cancer" is known medically as a malignant neoplasm. Cancer is a broad group of diseases involving upregulated cell growth. In cancer, cells (cancerous cells) divide and grow uncontrollably, forming malignant tumors, and invading nearby parts of the body. The cancer may also spread to more distant parts of the body through the lymphatic system or bloodstream. There are over 200 different known cancers that affect humans.

The term "malignant" or "malignancy" describes cells, groups of cells or tissues that constitute a neoplasm, are derived from a neoplasm or can be the origin of new neoplastic cells. The term is used to describe neoplastic cells in contrast to normal or healthy cells of a tissue. A malignant tumor contrasts with a non-cancerous benign tumor in that a malignancy is not self-limited in its growth, is capable of invading into adjacent tissues, and may be capable of spreading to distant tissues. A benign tumor has none of those properties. Malignancy is characterized by anaplasia, invasiveness, and metastasis as well as genome instability. The term "premalignant cells" refer to cells or tissue that is not yet malignant but is poised to become malignant.

The term "chemotherapy" refers to the treatment of cancer (cancerous cells) with one or more cytotoxic antineoplastic drugs ("chemotherapeutic agents" or "chemotherapeutic drugs") as part of a standardized regimen. Chemotherapy may be given with a curative intent or it may aim to prolong life or to palliate symptoms. It is often used in conjunction with other cancer treatments, such as radiation therapy, surgery, and/or hyperthermia therapy. Traditional chemotherapeutic agents act by killing cells that divide rapidly, one of the main properties of most cancer cells. This means that chemotherapy also harms cells that divide rapidly under normal circumstances, such as cells in the bone marrow, digestive tract, and hair follicles. This results in the most common side-effects of chemotherapy, such as myelosuppression (decreased production of blood cells, hence also immunosuppression), mucositis (inflammation of the lining of the digestive tract), and alopecia (hair loss).

The term "immune cell" or "immune effector cell" refers to a cell that may be part of the immune system and executes a particular effector function such as alpha-beta T cells, NK cells, NKT cells, B cells, innate lymphoid cells (ILC), cytokine induced killer (CIK) cells, lymphokine activated killer (LAK) cells, gamma-delta T cells, mesenchymal stem cells or mesenchymal stromal cells (MSC), monocytes or macrophages. Preferred immune cells are cells with cytotoxic effector function such as alpha-beta T cells, NK cells, NKT cells, ILC, CIK cells, LAK cells or gamma-delta T cells. "Effector function" means a specialized function of a cell, e.g. in a T cell an effector function may be cytolytic activity or helper activity including the secretion of cytokines.

The term "side-effects" refers to any complication, unwanted or pathological outcome of an immunotherapy with an antigen recognizing receptor that occurs in addition to the desired treatment outcome. The term "side-effect" preferentially refers to on-target off-tumor toxicity, that might occur during immunotherapy in case of presence of the target antigen on a cell that is an antigen-expressing non-target cell but not a diseased cell as described herein. A side-effect of an immunotherapy may be the developing of graft versus host disease.

The term "reducing side-effects" refers to the decrease of severity of any complication, unwanted or pathological outcome of an immunotherapy with an antigen recognizing receptor such as toxicity towards an antigen-expressing non-target cell. "Reducing side-effects" also refers to measures that decrease or avoid pain, harm or the risk of death for the patient during the immunotherapy with an antigen recognizing receptor.

The term "combination immunotherapy" refers to the concerted application of two therapy approaches e.g. therapy approaches known in the art for the treatment of disease such as cancer. The term "combination immunotherapy" may also refer to the concerted application of an immunotherapy such as the treatment with an antigen recognizing receptor and another therapy such as the transplantation of hematopoietic cells e.g. hematopoietic cells resistant to recognition by the antigen recognizing receptor.

Expression of an antigen on a cell means that the antigen is sufficient present on the cell surface of said cell, so that it can be detected, bound and/or recognized by an antigen-recognizing receptor.

The term "hematopoietic cells", refers to a population of cells of the hematopoietic lineage capable of hematopoiesis which include but is not limited to hematopoietic stem cells and/or hematopoietic progenitor cells (i.e., capable to proliferate and at least partially reconstitute different blood cell types, including erythroid cells, lymphocytes, and myelocytes). The term "hematopoietic cells" as used herein also includes the cells that are differentiated from the hematopoietic stem cells and/or hematopoietic progenitor cells to form blood cells (i.e. blood cell types, including erythroid cells, lymphocytes, and myelocytes).

A hematopoietic cell resistant to recognition of an antigen by an antigen-recognizing receptor means that said cell cannot as easily be detected, bound and/or recognized by an antigen-recognizing receptor specific for said antigen or that the detection, binding and/or recognizing is impaired, so that no or reduced side-effects can be observed during a immunotherapy using the cells of the present invention.

An antigen is said to be "resistant" to recognition by a receptor or an antibody if it is expressed in a form, in a manner, or at a density that inhibits or reduces binding of the receptor. Either it binds at least 10-fold (and preferably 10-fold to 1000-fold, more preferably 1000 fold to 100,000 fold and most preferably 100,000 to 10,000,000 fold) less receptor under the same conditions as the wild-type antigen does when presented under normal conditions, or it binds the receptor with at least 10-fold (and preferably 10-fold to 1000-fold, more preferably 1000 fold to 100,000 fold and most preferably 100,000 to 10,000,000 fold) lower affinity. In certain embodiments of the invention, the antigen is recombinantly modified to inhibit or reduce receptor binding. Typically, an antigen modified in this way is over 90% identical to the wild type isoform at the amino acid level, but has been recombinantly introduced with at least one, two, three, five, or more than five altered amino acids, additions, or amino acid deletions that change primary, secondary, or tertiary protein structure so as to inhibit or reduce receptor recognition. In other cases the antigen can be modified (e.g. shortened, elongated or truncated) to eliminate the binding motif. However the original functionality of the target antigen is preferably not affected by the modification.

By way of illustration, the hematopoietic cell resistant to recognition of said antigen by an antigen-recognizing receptor specific for said antigen which is used in the method or system of the present invention can be generated for example by using an antigen 1) which has at least one splice variant within the extracellular domain of said antigen suitable for generating different epitopes for antigen binding domains, or
2) which has at least a natural polymorphic form within the extracellular domain of said antigen suitable for generating different epitopes for antigen binding domains; or
3) which can be modified to a non-natural polymorphic form within the extracellular domain of said antigen suitable for generating different epitopes for antigen binding domains, wherein said non-natural polymorphic form does not alter or affect the natural function of said antigen on the cells; or
4) which can be deleted (e.g. knocked out) without alteration or affecting the natural function of the hematopoietic cell.

The result is a deviation in said antigen so that the hematopoietic cell cannot be recognized by said antigen-recognizing receptor anymore or can be recognized in a alleviated form only.

The term "fratricide" refers to the observation that the antigen associated with disease may be, in addition to diseased cells, present on immune effector cells engineered, such as T cells expressing an antigen-recognizing receptor, such as a CAR. In that case the side-effects of the antigen recognizing receptor will affect the immune effector cells engineered to express the antigen recognizing receptor. Such side-effect is also known in the art as fratricide.

In general, the term "receptor" refers to a biomolecule that may be soluble or attached to the cell surface membrane and specifically binds a defined structure that may be attached to a cell surface membrane or soluble. Receptors include but are not restricted to antibodies and antibody like structures, adhesion molecules, transgenic or naturally occurring TCRs or CARS. In specific, the term "antigen-recognizing receptor" as used herein may be a membrane bound or soluble receptor such as a natural TCR, a transgenic TCR, a CAR, a scFv or multimers thereof, a Fab-fragment or multimers thereof, an antibody or multimers thereof, a bi-specific T cell enhancer (BiTE), a diabody, or any other molecule that can execute specific binding with high affinity.

The term "antigen" refers to a molecular entity that may be soluble or cell membrane bound in particular but not restricted to molecular entities that can be recognized by means of the adaptive immune system including but not restricted to antibodies or TCRs, or engineered molecules including but not restricted to transgenic TCRs, CARS, scFvs or multimers thereof, Fab-fragments or multimers thereof, antibodies or multimers thereof, single chain antibodies or multimers thereof, or any other molecule that can execute binding to a structure with high affinity.

The term "target" or "target antigen" refers to any cell surface protein, glycoprotein, glycolipid or any other structure present on the surface of the target cell. The term also refers to any other structure present on target cells in particular but not restricted to structures that can be recognized by means of the adaptive immune system including but not restricted to antibodies or TCRs, or engineered molecules including but not restricted to transgenic TCRs, CARS, scFvs or multimers thereof, Fab-fragments or multimers thereof, antibodies or multimers thereof, single chain antibodies or multimers thereof, or any other molecule that can execute binding to a structure with high affinity.

The term "target cells" as used herein refers to cells which are recognized by the antigen-recognizing receptor which is or will be applied to the individual.

The term "antigen-expressing non-target cell" as used herein refers to the healthy cells (non-diseases cells) of an individual treated with the method of the present invention, which express the same antigen as the target cells. The recognition of said antigen on the antigen-expressing non-target cells is not desired and may lead to complication (side-effects) on treatment in state of the art immunotherapy.

The terms "specifically binds" or "specific for" or "specifically recognize" with respect to an antigen-recognizing receptor refer to an antigen-binding domain of said antigen-recognizing receptor which recognizes and binds to a specific antigen, but does not substantially recognize or bind other molecules in a sample. An antigen-binding domain that binds specifically to an antigen from one species may bind also to that antigen from another species. This cross-species reactivity is not contrary to the definition of that antigen-binding domain as specific. An antigen-binding domain of an antigen-recognizing receptor that specifically binds to an antigen may bind also to different allelic forms of the antigen (allelic variants, splice variants, isoforms etc.). This cross reactivity is not contrary to the definition of that antigen-binding domain as specific as long as these different allelic forms of the antigen do not take part in the intended derivation of the antigen needed for the generation of the resistance of the hematopoietic cells to the antigen as used in the present invention.

The term "system for use in immunotherapy" as used herein refers to the constellation that two kinds of compositions are needed to perform the combined immunotherapy as disclosed herein. Therefore, the system (or set or kit or the combination of compositions) comprises
  a) an antigen-recognizing receptor wherein said antigen-recognizing receptor specifically recognizes an antigen on target cells in said individual;
  b) hematopoietic cells resistant to recognition of said antigen by said antigen-recognizing receptor.

"Chimeric antigen receptor" or "CAR" refer to engineered receptors, which graft an antigen specificity onto cells, for example T cells. The CARs of the invention comprise an antigen binding domain also known as antigen targeting region, an extracellular spacer domain or hinge region, a transmembrane domain and at least one intracellular signaling domain or a least one co-stimulatory domain and at least one intracellular signaling domain.

In general, a CAR may comprise an extracellular domain (extracellular part) comprising the antigen binding domain, a transmembrane domain and an intracellular signaling domain. The extracellular domain may be linked to the transmembrane domain by a linker. The extracellular domain may also comprise a signal peptide.

A "signal peptide" refers to a peptide sequence that directs the transport and localization of the protein within a cell, e.g. to a certain cell organelle (such as the endoplasmic reticulum) and/or the cell surface.

An "antigen binding domain" refers to the region of the CAR that specifically binds to an antigen (and thereby is able to target a cell containing an antigen). The CARS of the invention may comprise one or more antigen binding domains. Generally, the targeting regions on the CAR are extracellular. The antigen binding domain may comprise an antibody or a fragment thereof. The antigen binding domain may comprise, for example, full length heavy chain, Fab fragments, single chain Fv (scFv) fragments, divalent single chain antibodies or diabodies. Any molecule that binds specifically to a given antigen such as affibodies or ligand binding domains from naturally occurring receptors may be used as an antigen binding domain. Often the antigen binding domain is a scFv. Normally, in a scFv the variable portions of an immunoglobulin heavy chain and light chain are fused by a flexible linker to form a scFv. Such a linker may be for example the "$(G_4/S_1)_3$-linker".

In some instances, it is beneficial for the antigen binding domain to be derived from the same species in which the CAR will be used in. For example, when it is planned to use it therapeutically in humans, it may be beneficial for the antigen binding domain of the CAR to comprise a human or humanized antibody or fragment thereof. Human or humanized antibodies or fragments thereof can be made by a variety of methods well known in the art.

"Spacer" or "hinge" as used herein refers to the hydrophilic region which is between the antigen binding domain and the transmembrane domain. The CARs of the invention may comprise an extracellular spacer domain but is it also possible to pass such a spacer. The spacer may include Fc fragments of antibodies or fragments thereof, hinge regions of antibodies or fragments thereof, CH2 or CH3 regions of antibodies, accessory proteins, artificial spacer sequences or combinations thereof. A prominent example of a spacer is the CD8alpha hinge.

The transmembrane domain of the CAR can be derived from any desired natural or synthetic source for such domain. When the source is natural the domain may be derived from any membrane-bound or transmembrane protein. The transmembrane domain may be derived for example from CD8alpha or CD28. When the key signaling and antigen recognition modules are on two (or even more) polypeptides then the CAR may have two (or more) transmembrane domains. Splitting key signaling and antigen recognition modules enables for a small molecule-dependent, titratable and reversible control over CAR cell expression (Wu et al, 2015, Science 350: 293-303) due to small molecule-dependent heterodimerizing domains in each polypeptide of the CAR.

The cytoplasmic domain or the intracellular signaling domain of the CAR is responsible for activation of at least one of the normal effector functions of the immune cell in which the CAR is expressed. "Effector function" means a specialized function of a cell, e.g. in a T cell an effector function may be cytolytic activity or helper activity including the secretion of cytokines. The intracellular signaling domain refers to the part of a protein which transduces the effector function signal and directs the cell expressing the CAR to perform a specialized function.

The intracellular signaling domain may include any complete or truncated part of the intracellular signaling domain of a given protein sufficient to transduce the effector function signal. Prominent examples of intracellular signaling domains for use in the CARs include the cytoplasmic sequences of the T cell receptor (TCR) and co-receptors that act in concert to initiate signal transduction following antigen receptor engagement.

Generally, T cell activation can be mediated by two distinct classes of cytoplasmic signaling sequences, firstly those that initiate antigen-dependent primary activation through the TCR (primary cytoplasmic signaling sequences) and secondly those that act in an antigen-independent manner to provide a secondary or co-stimulatory signal (secondary cytoplasmic signaling sequences, costimulatory signaling domain). Therefore, an intracellular signaling domain of a CAR may comprise a primary cytoplasmic signaling domain and/or a secondary cytoplasmic signaling domain.

Primary cytoplasmic signaling sequences that act in a stimulatory manner may contain ITAMs (immunoreceptor tyrosine-based activation motifs signaling motifs). Examples of ITAM containing primary cytoplasmic signaling sequences often used in CARS are that are those derived from TCR zeta (CD3 zeta), FcR gamma, FcR beta, CD3 gamma, CD3 delta, CD3 epsilon, CD5, CD22, CD79a, CD79b, and CD66d. Most prominent is sequence derived from CD3 zeta.

The cytoplasmic domain of the CAR can be designed to comprise the CD3-zeta signaling domain by itself or combined with any other desired cytoplasmic domain(s). The cytoplasmic domain of the CAR can comprise a CD3 zeta chain portion and a costimulatory signaling region. The costimulatory signaling region refers to a part of the CAR comprising the intracellular domain of a costimulatory molecule. A costimulatory molecule is a cell surface molecule other than an antigen receptor or their ligands that is required for an efficient response of lymphocytes to an antigen. Examples for a costimulatory molecule are CD27, CD28, 4-1BB (CD137), OX40, CD30, CD40, PD-1, ICOS, lymphocyte function-associated antigen-1 (LFA-1), CD2, CD7, LIGHT, NKG2C, B7-H3. The cytoplasmic signaling sequences within the cytoplasmic signaling part of the CAR may be linked to each other in a random or specified order. A short oligo- or polypeptide linker, which is preferably between 2 and 10 amino acids in length, may form the linkage. A prominent linker is the glycine-serine doublet.

As an example, the cytoplasmic domain may comprise the signaling domain of CD3-zeta and the signaling domain of CD28. In another example the cytoplasmic domain may comprise the signaling domain of CD3-zeta and the signaling domain of CD27. In an further example, the cytoplasmic domain may comprise the signaling domain of CD3-zeta, the signaling domain of CD28, and the signaling domain of CD27.

As aforementioned either the extracellular part or the transmembrane domain or the cytoplasmic domain of a CAR may also comprise a heterodimerizing domain for the aim of splitting key signaling and antigen recognition modules of the CAR.

The CAR of the invention may be designed to comprise any portion or part of the above-mentioned domains as described herein in any combination resulting to a functional CAR.

To qualify as a "chimeric antigen receptor" in the embodiments of the invention claimed below, a CAR minimally has at least an antigen-specific variable region (typically a single chain variable region comprised of antibody heavy and light chain variable regions) linked to a T cell signaling domain: typically an intracellular domain of a T-cell receptor, exemplified by (but not limited to) the zeta domain of CD3. Upon binding of the antigen-specific region to the corresponding antigen, the T cell signaling domain mediates a T cell function in the host cell (such as cytotoxicity). The CAR may optionally but does not necessarily comprise additional domains, such as a linker, a transmembrane domain, and other intracellular signaling elements as described above.

The term "genetic modification" or genetically modified" refers to the alteration of the nucleic acid content including but not restricted to the genomic DNA of a cell. This includes but is not restricted to the alteration of a cells genomic DNA sequence by introduction exchange or deletion of single nucleotides or fragments of nucleic acid sequence. The term also refers to any introduction of nucleic acid into a cell independent of whether that leads to a direct or indirect alteration of the cells genomic DNA sequence or not.

The terms "engineered cell" and "genetically modified cell" as used herein can be used interchangeably. The terms mean containing and/or expressing a foreign gene or nucleic acid sequence, which in turn modifies the genotype or phenotype of the cell or its progeny. Especially, the terms refer to the fact that cells can be manipulated by recombinant methods well known in the art to express stably or transiently peptides or proteins, which are not expressed in these cells in the natural state. Genetic modification of cells may include but is not restricted to transfection, electroporation, nucleofection, transduction using retroviral vectors, lentiviral vectors, non-integrating retro- or lentiviral vectors, transposons, designer nucleases including zinc finger nucleases, TALENs or CRISPR/Cas.

The term "therapeutic effective amount" means an amount, which provides a therapeutic benefit.

Immunotherapy is a medical term defined as the "treatment of disease by inducing, enhancing, or suppressing an immune response". Immunotherapies designed to elicit or amplify an immune response are classified as activation immunotherapies, while immunotherapies that reduce or suppress are classified as suppression immunotherapies. Cancer immunotherapy as an activating immunotherapy attempts to stimulate the immune system to reject and destroy tumors. Adoptive cell transfer uses cell-based cytotoxic responses to attack cancer cells. Immune cells such as T cells that have a natural or genetically engineered reactivity to a patient's cancer are generated in vitro and then transferred back into the cancer patient.

The term "treatment" as used herein means to reduce the frequency or severity of at least one sign or symptom of a disease.

As used herein, the term "individual" refer to an animal. Preferentially, the individual is a mammal such as mouse, rat, cow, pig, goat, chicken dog, monkey or human. More preferentially, the individual is a human. The individual may be an individual suffering from a disease such as cancer (a patient), but the subject may be also a healthy subject.

The amino acid sequences of anti-human CD20 $V_H$, anti-human CD20 $V_L$, are given in SEQ ID NO:1 and SEQ ID NO:2, respectively (in the one-letter code of amino acids). The amino acid sequences (proteins, polypeptides) as given in the SEQ ID NO:1 and SEQ ID NO:2 refer to all constellations of the respective amino acid sequence which retains the intended function of the respective amino acid sequence as defined herein. In other words, the divergences to the SEQ ID No:1 and SEQ ID NO:2, respectively, should not affect their potential as binding specifically to the antigen CD20 and/or being a functional CAR. Therefore, the amino acid sequences of SEQ ID NO:1 and SEQ ID NO:2 can be the full length amino acid sequence of the SEQ ID NO:1 and SEQ ID NO:2, respectively. It can also be a variant thereof which have some amino acids deleted, added or replaced while still retaining the intended function as described herein. Therefore, included in this definition are variants of the amino acid sequences in SEQ ID NO: 1 and SEQ ID NO:2, respectively, such as amino acid sequences essentially similar to SEQ ID NO: 1 and SEQ ID NO:2, respectively, having a sequence identity of at least 70%, or at least 75%, 80%, 85%, 90%, 95%, 97%, 98% or 99% at the amino acid sequence level. In the context of the present invention, "sequence identity" may be determined using pairwise alignments using alignments programs for amino acid sequences well known to the art.

EXAMPLES

Example 1: Targeting the CD20 Antigen with a CD20-Recognizing CAR Expressed in T Cells where 2 Amino Acids of the Wild Type CD20 Antigen Have Been Mutated to Abrogate CD20 Recognition by the Antigen Recognizing Receptor In a first instance we have used HEK 293 T cells to overexpress several variants of the human CD20 antigen (the sequences were synthesized by DNA 2.0 and cloned into the plasmid pMACS LNGFR-IRES of Miltenyi Biotec). FIG. 2 shows how mutations of amino acids A into S at position 170 and P into S at positions 172 of the wild type human CD20 antigen (SEQ ID NO:3) abrogate binding of the anti-CD20 antibody clone 2H7.

A CAR encoding the antigen-recognizing receptor of the 2H7 (see SEQ ID NO 1 and 2) with an IgG1 extracellular spacer, a CD8 transmembrane and an intracellular signaling domain of 4-1BB-CD3 zeta was generated and cloned into a lentiviral vector (provided by Lentigen Technology, Inc., USA). Human T cells were activated with MACS GMP TransAct kit (Miltenyi Biotec according to the manufacturers recommendations, transduced with the CD20 CAR encoding lentiviral vector at a multiplicity of infection of 2 and expanded in TexMACS medium with 20 ng/ml human IL-2 (Miltenyi Biotec) for 14 days. The CAR transduced T cells where then co-cultured for 24 hours at a ratio of 1 to 1 with the target cells indicated in FIG. 2. FIG. 3 shows the measurements of GM-CSF and IL-2 expressed by the CART cells in the supernatant of the culture (using the MACSPlex™ cytokine measurement system of Miltenyi Biotec). The CAR T cells specifically produce cytokines in the presence of HEK-293 T cells that express the wild type CD20 antigen but not when the HEK-293 T cells express the mutant CD20 antigen.

Thus, using minor gene-editing, it is possible to maintain expression of the CD20 antigen while abrogating recognition by the T cells expressing the antigen recognizing receptor.

Several methods can be used to edit genes. In order to illustrate the possibility to switch human CD20 wild type expression to expression of the mutant form, we have electroporated the Raji cell line (which naturally expresses wild type CD20) with the Cas9 nuclease, the indicated guide RNA (see FIG. 4 and SEQ ID NO:4 to SEQ ID NO:9) and a transfection control encoding GFP using the plasmids. FIG. 4 shows that the best "loss" of CD20 APC staining was obtained when using the gRNA2 (15% of the GFP transfected cells).

FIG. 4 represents the proof of principle that an epitope of an antigen expressed by cells can be altered. Thus a target cell can become a non-target for a given antigen-recognizing receptor expressed by a given effector cell.

In this example, the antigen CD20 is not expressed by the T cells therefore no gene-editing of the antigen in the T cells would be necessary in order to avoid fratricide. In this application, hematopoietic stem cells (of the same T cell donor) would however be edited (similarly to FIG. 4) in order for the progeny of the HSCs to not be recognized by the CD20 CAR T cells. Thus the patient with wild type CD20 positive target cells such as tumor cells but also healthy B cells expressing the wild type CD20 would be depleted of all original CD20 positive cells (tumor and healthy B cells) but healthy B cells with mutated CD20 antigen would be able to repopulate the patient therefore reducing sustained B cell aplasia.

Example 2: Use of an Antigen Recognizing Receptor to Target an Antigen Present on the Majority of Haematopoietic Cells Including T Cells In this example we have taken advantage of the polymorphism of CD45 in mouse models. As indicated in FIG. 5, the amino acid differences guiding the polymorphism of CD45.1 and CD45.2 isoforms in C57BL/6 mice is known. One can generate antibodies specifically recognizing the 2 isoforms separately. Such antibodies exist that recognize either the CD45.2 or the CD45.1 isoform of the mouse CD45 surface molecule. However, in this model it is unknown, which epitopes the existing antibodies recognize. We have therefore used plasmids encoding the sequence of three different mutants of the CD45.2 isoform or the wild type CD45.2 to force expression of said antigens in the HEK-293T cell line. As indicated in FIG. 6, mutation of the amino acid K in position 277 to E allows the anti-CD45.1 antibody to bind the antigen and abrogates the binding of anti-CD45.2 antibody. The 2 other constructs maintain specificity for the CD45.2 antibody.

Therefore it is possible to use the anti-CD45.2 antibody to generate an anti-CD45.2 recognizing CAR that would be "blind" to the K in position 277 to E mutation, or vice versa to use the anti-CD45.1 antibody to generate an anti-CD45.1 recognizing CAR that would be "blind" to the K in position 277.

Figure 7:
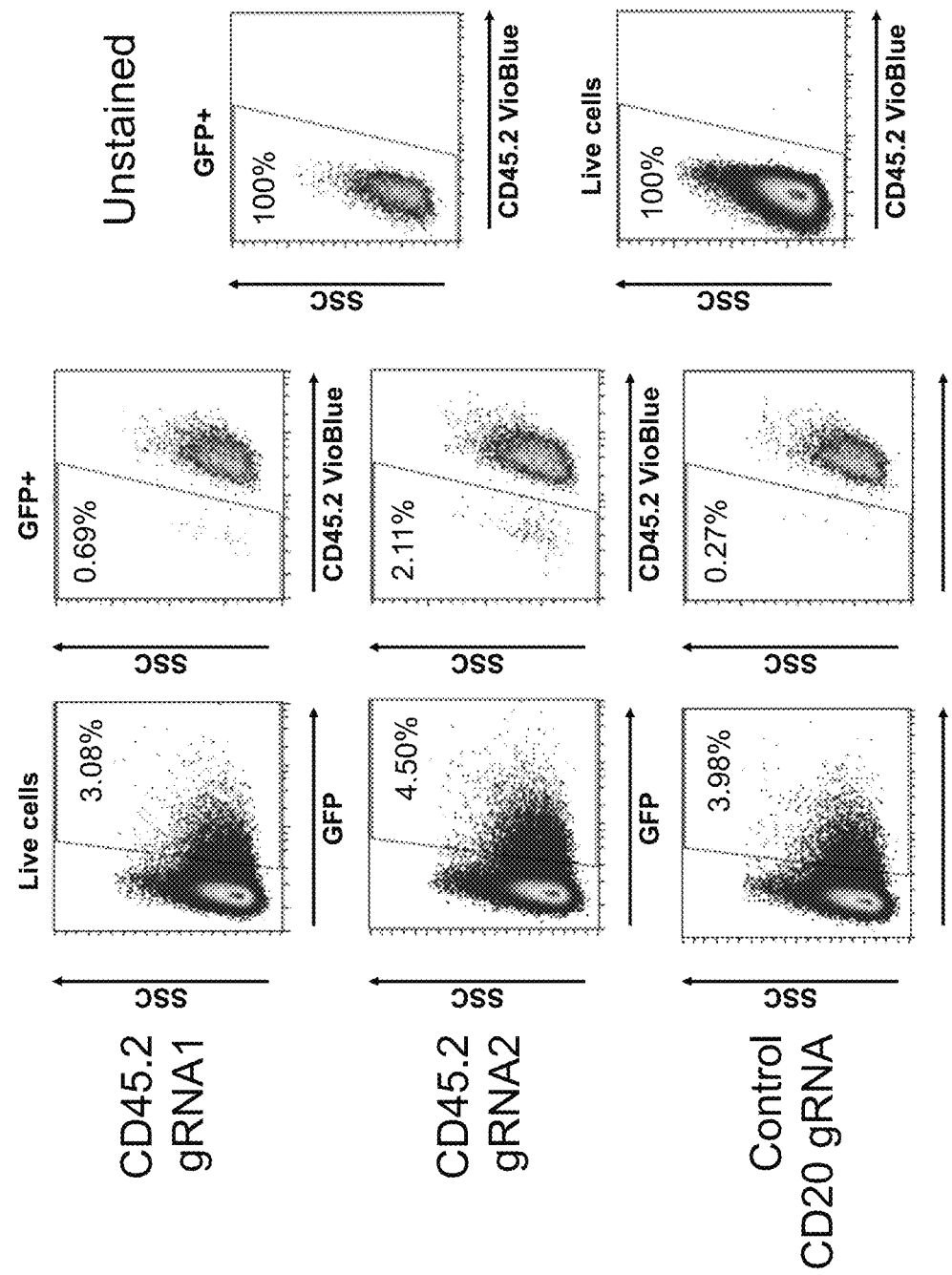
FIG. 7: Gene-editing of the CD45.2 antigen using designer nucleases in order to abrogate recognition of the antigen by the antigen recognizing anti-CD45.2 antibody. The 1881 cell line naturally expressing CD45.2 was transfected by co-electroporation with 3 plasmids; one encoding the green fluorescent protein (as transfection control), one encoding the guide RNA sequences (gRNA 1 and 2 or for control CD20 gRNA1) (see SEQ ID NO:10 and SEQ ID NO:11, or SEQ ID NO:12 and SEQ ID NO:13) and one encoding the nuclease Cas9. 4 days after gene-editing, the CD45.1 expression of the GFP positive 1881 cells was analyzed by flow cytometry using the anti-CD45.2 antibody. The 2 dot plots on the right represent controls as indicated for a sample not incubated with anti-CD45.2 antibody.

Similarly as in example 1 and as shown in FIG. 7, the CD45.2 expressed at the surface of the 1881 cell line could be, in part, gene-edited with the gRNA SEQ ID NO:12 and SEQ ID NO:13 and the cas9 nuclease to not be recognized by the CD45.2 antibody.

FIG. 8 represents known polymorphisms of the human CD45 antigen. Several forms are associated with disease while others are not.

Example 3: Editing of Antigens Present in Malignancies Associated to Early Precursors of HSCs and/or HSCs In this example the antigens associated to the disease are also present on healthy HSCs but not on T cells. Polymorphisms of antigens such as CD34 or CD133 are defined, and antigen-recognizing receptors are defined that can specifically target the wild type antigens but not specific mutations of the wild type antigen. As in example 3, healthy HSCs are purified (e.g. using a cell sorter and markers capable of differentiating healthy HSCs from the diseased or the malignant ones), gene edited and infused into the patient. T cells from the same patient are then modified to express the antigen-recognizing receptor without the need to be edited for the antigen.

SEQUENCE LISTING

```
heavy chain variable domain (V_H) of anti-human CD20
                                           SEQ ID NO: 1
MAQVKLQESG AELVKPGASV KMSCKASGYT FTSYNMHWVK
QTPGQGLEWI GAIYPGNGDT SYNQKFKGKA TLTADKSSST
AYMQLSSLTS EDSADYYCAR SNYYGSSYWF FDVWGQGTTV TVSS light chain variable domain (V_L) of anti-human CD20
                                           SEQ ID NO: 2
DIELTQSPTI LSASPGEKVT MTCRASSSVN YMDWYQKKPG
SSPKPWIYAT SLASGVPARF SGSGSGTSYS TISRVEAEDA
ATYYCQQWSF NPPTFGGGTK LEIK wild-type human CD20
                                           SEQ ID NO: 3
MTTPRNSVNG TFPAEPMKGP IAMQSGPKPL FRRMSSLVGP
TQSFFMRESK TLGAVQIMNG LFHIALGGLL MIPAGIYAPI
CVTVWYPLWG GIMYIISGSL LAATEKNSRK CLVKGKMIMN
SLSLFAAISG MILSIMDILN IKISHFLKME SLNFIRAHTP
YINIYNCEPA NPSEKNSPST QYCYSIQSLF LGILSVMLIF
AFFQELVIAG IVENEWKRTC SRPKSNIVLL SAEEKKEQTI
EIKEEVVGLT ETSSQPKNEE DIEIIPIQEE EEEETETNFP
EPPQDQESSP IENDSSP Target site 1 Rev G19nGG (CD20 gRNA1) Oligo Fw
                                           SEQ ID NO: 4
ACCGATGG GGAGTTTTTC TCAGAG Target site 1 Rev G19nGG (CD20 gRNA1) Oligo Rev
                                           SEQ ID NO: 5
AAAACTCTGA GAAAAACTCC CCATCG Target site 2 Rev G19nGG (CD20 gRNA2) Oligo Fw
                                           SEQ ID NO: 6
ACACCGTAAC AGTATTGGGT AGATGG Target site 2 Rev G19nGG (CD20 gRNA2) Oligo Rev
                                           SEQ ID NO: 7
AAAACCATCT ACCCAATACT GTTACG Target site 5 Rev G17nGG (CD20 gRNA3) Oligo Fw
                                           SEQ ID NO: 8
ACACCGTATG CTGTAACAGT ATTG Target site 5 Rev G17nGG (CD20 gRNA3) Oligo Rev
                                           SEQ ID NO: 9
AAAACAATAC TGTTACAGCA TACG Target site 1 Rev G18nGG (CD45.2 gRNA1) Oligo Fw
                                           SEQ ID NO: 10
ACACCGTTGC ATTTTCTGAA ATCAG Target site 1 Rev G18nGG (CD45.2 gRNA1) Oligo Rev
                                           SEQ ID NO: 11
AAAACTGATT TCAGAAAATG CAACG Target site 2 Fw G19nGG (CD45.2 gRNA2) Oligo Fw
                                           SEQ ID NO: 12
ACACCGGCTA ATACTTCAAT TTGTTG Target site 2 Fw G19nGG (CD45.2 gRNA2) Oligo Rev
                                           SEQ ID NO: 13
AAAACAACAA ATTGAAGTAT TAGCCG
```

While the invention has been described with reference to the specific embodiments, changes can be made and equivalents can be substituted to adapt to a particular context or intended use, thereby achieving benefits of the invention without departing from the scope of what is claimed.

The invention claimed is:

1. A method for immunotherapy of a patient in need thereof, comprising administering a combination of immune effector cells and non-target hematopoietic cells to the patient, comprising:
   (a) obtaining a population of immune effector cells,
      wherein the immune effector cells are derived from cells of the patient or an allogeneic effector cell donor and modified to express a chimeric recombinant antigen-recognizing receptor (CAR) that binds an extracellular epitope of a target antigen,
      wherein the target antigen is a cell surface antigen expressed on target cells and on cells of a non-target hematopoietic cell subpopulation of the patient;
   (b) obtaining cells of the non-target hematopoietic cell subpopulation from the patient or an allogeneic cell donor;
   (c) producing a progeny cell population from the non-target hematopoietic cell subpopulation by a process that comprises gene-editing the cells obtained in step (b) and obtaining progeny of the gene-edited cells, wherein said gene-editing results in expression of an altered form of the target antigen by cells of the progeny cell population,
      wherein the altered form of the target antigen has at least one amino acid substitution or deletion in the extracellular epitope bound by the CAR, wherein the CAR has lower binding affinity to the altered form of the target antigen compared with the target antigen expressed on the immune effector cells obtained in step (a);
   (d) administering the immune effector cells and cells of the progeny cell population to the patient.

2. The method of claim 1 wherein the immune effector cells are CAR T cells produced by a process that comprises genetically modifying T cells obtained in step (a).

3. The method of claim 1 wherein the immune effector cells are CAR NK cells produced by a process that comprises genetically modifying NK cells obtained in step (a).

4. The method of claim 1 wherein the target cells are cancer cells that express the target antigen.

5. The method of claim 1 wherein the immune effector cells are administered to the subject before or after the cells of the progeny cell population are administered.

6. The method of claim 1 wherein the extracellular domain of the target antigen is modified by one amino acid substitution or deletion to produce the altered form of the target antigen.

7. The method of claim 1 wherein the extracellular domain of the target antigen is modified by two amino acid substitutions or deletions to produce the altered form of the target antigen.

8. The method of claim 1 wherein the extracellular domain of the target antigen is modified by three amino acid substitutions or deletions to produce the altered form of the target antigen.

9. The method of claim 1 wherein the extracellular domain of the target antigen is modified by five amino acid substitutions or deletions to produce the altered form of the target antigen.

10. The method of claim 1 wherein the extracellular domain of the target antigen is modified by a deletion of more than five amino acid substitutions or deletions to produce the altered form of the target antigen.

11. The method of claim 1 wherein the target antigen is CD11a, CD18, CD19, CD20, CD31, CD34, CD44, CD45, CD47, CD51, CD58, CD59, CD63, CD97, CD99, CD100, CD102, CD123, CD127, CD133, CD135, CD157, CD172b, CD217, CD300a, CD305, CD317 or CD321.

* * * * *

SEQUENCE LISTING

```
<160> NUMBER OF SEQ ID NOS: 13

<210> SEQ ID NO 1
<211> LENGTH: 124
<212> TYPE: PRT
<213> ORGANISM: Artificial Sequence
<220> FEATURE:
<223> OTHER INFORMATION: heavy chain variable domain (VH) of anti-human
      CD20

<400> SEQUENCE: 1

Met Ala Gln Val Lys Leu Gln Glu Ser Gly Ala Glu Leu Val Lys Pro
```

```
            1               5                  10                 15
        Gly Ala Ser Val Lys Met Ser Cys Lys Ala Ser Gly Tyr Thr Phe Thr
                        20                  25                  30

Ser Tyr Asn Met His Trp Val Lys Gln Thr Pro Gly Gln Gly Leu Glu
                        35                  40                  45

Trp Ile Gly Ala Ile Tyr Pro Gly Asn Gly Asp Thr Ser Tyr Asn Gln
                50                  55                  60

Lys Phe Lys Gly Lys Ala Thr Leu Thr Ala Asp Lys Ser Ser Ser Thr
        65                  70                  75                  80

Ala Tyr Met Gln Leu Ser Ser Leu Thr Ser Glu Asp Ser Ala Asp Tyr
                        85                  90                  95

Tyr Cys Ala Arg Ser Asn Tyr Tyr Gly Ser Ser Tyr Trp Phe Phe Asp
                        100                 105                 110

Val Trp Gly Gln Gly Thr Thr Val Thr Val Ser Ser
                        115                 120
```

<210> SEQ ID NO 2
<211> LENGTH: 104
<212> TYPE: PRT
<213> ORGANISM: Artificial Sequence
<220> FEATURE:
<223> OTHER INFORMATION: light chain variable domain (VL) of anti-human CD20

<400> SEQUENCE: 2

```
        Asp Ile Glu Leu Thr Gln Ser Pro Thr Ile Leu Ser Ala Ser Pro Gly
        1               5                   10                  15

Glu Lys Val Thr Met Thr Cys Arg Ala Ser Ser Ser Val Asn Tyr Met
                        20                  25                  30

Asp Trp Tyr Gln Lys Lys Pro Gly Ser Ser Pro Lys Pro Trp Ile Tyr
                        35                  40                  45

Ala Thr Ser Leu Ala Ser Gly Val Pro Ala Arg Phe Ser Gly Ser Gly
                        50                  55                  60

Ser Gly Thr Ser Tyr Ser Thr Ile Ser Arg Val Glu Ala Glu Asp Ala
        65                  70                  75                  80

Ala Thr Tyr Tyr Cys Gln Gln Trp Ser Phe Asn Pro Pro Thr Phe Gly
                        85                  90                  95

Gly Gly Thr Lys Leu Glu Ile Lys
                        100
```

<210> SEQ ID NO 3
<211> LENGTH: 297
<212> TYPE: PRT
<213> ORGANISM: Homo sapiens

<400> SEQUENCE: 3

```
        Met Thr Thr Pro Arg Asn Ser Val Asn Gly Thr Phe Pro Ala Glu Pro
        1               5                   10                  15

Met Lys Gly Pro Ile Ala Met Gln Ser Gly Pro Lys Pro Leu Phe Arg
                        20                  25                  30

Arg Met Ser Ser Leu Val Gly Pro Thr Gln Ser Phe Phe Met Arg Glu
                        35                  40                  45

Ser Lys Thr Leu Gly Ala Val Gln Ile Met Asn Gly Leu Phe His Ile
                        50                  55                  60

Ala Leu Gly Gly Leu Leu Met Ile Pro Ala Gly Ile Tyr Ala Pro Ile
        65                  70                  75                  80

Cys Val Thr Val Trp Tyr Pro Leu Trp Gly Gly Ile Met Tyr Ile Ile
```

|   |   |   | 85 |   |   |   | 90 |   |   |   | 95 |   |
|---|---|---|---|---|---|---|---|---|---|---|---|---|

Ser Gly Ser Leu Leu Ala Ala Thr Glu Lys Asn Ser Arg Lys Cys Leu
               100                 105               110

Val Lys Gly Lys Met Ile Met Asn Ser Leu Ser Leu Phe Ala Ala Ile
     115                 120                 125

Ser Gly Met Ile Leu Ser Ile Met Asp Ile Leu Asn Ile Lys Ile Ser
 130                 135                 140

His Phe Leu Lys Met Glu Ser Leu Asn Phe Ile Arg Ala His Thr Pro
145               150                 155               160

Tyr Ile Asn Ile Tyr Asn Cys Glu Pro Ala Asn Pro Ser Glu Lys Asn
               165                 170               175

Ser Pro Ser Thr Gln Tyr Cys Tyr Ser Ile Gln Ser Leu Phe Leu Gly
         180                 185               190

Ile Leu Ser Val Met Leu Ile Phe Ala Phe Phe Gln Glu Leu Val Ile
     195                 200                 205

Ala Gly Ile Val Glu Asn Glu Trp Lys Arg Thr Cys Ser Arg Pro Lys
 210                 215                 220

Ser Asn Ile Val Leu Leu Ser Ala Glu Glu Lys Lys Glu Gln Thr Ile
225               230                 235               240

Glu Ile Lys Glu Glu Val Val Gly Leu Thr Glu Thr Ser Ser Gln Pro
               245                 250               255

Lys Asn Glu Glu Asp Ile Glu Ile Ile Pro Ile Gln Glu Glu Glu Glu
         260                 265               270

Glu Glu Thr Glu Thr Asn Phe Pro Glu Pro Pro Gln Asp Gln Glu Ser
     275                 280                 285

Ser Pro Ile Glu Asn Asp Ser Ser Pro
 290                 295

<210> SEQ ID NO 4
<211> LENGTH: 26
<212> TYPE: DNA
<213> ORGANISM: Artificial Sequence
<220> FEATURE:
<223> OTHER INFORMATION: Target site 1 Rev G19nGG (CD20 gRNA1) Oligo Fw

<400> SEQUENCE: 4
acaccgatgg ggagttttc tcagag                                        26

<210> SEQ ID NO 5
<211> LENGTH: 26
<212> TYPE: DNA
<213> ORGANISM: Artificial Sequence
<220> FEATURE:
<223> OTHER INFORMATION: Target site 1 Rev G19nGG (CD20 gRNA1) Oligo Rev

<400> SEQUENCE: 5
aaaactctga gaaaaactcc ccatcg                                        26

<210> SEQ ID NO 6
<211> LENGTH: 26
<212> TYPE: DNA
<213> ORGANISM: Artificial Sequence
<220> FEATURE:
<223> OTHER INFORMATION: Target site 2 Rev G19nGG (CD20 gRNA2) Oligo Fw

<400> SEQUENCE: 6
acaccgtaac agtattgggt agatgg                                        26

<210> SEQ ID NO 7

-continued

<210> SEQ ID NO 7
<211> LENGTH: 26
<212> TYPE: DNA
<213> ORGANISM: Artificial Sequence
<220> FEATURE:
<223> OTHER INFORMATION: Target site 2 Rev G19nGG (CD20 gRNA2) Oligo Rev

<400> SEQUENCE: 7
aaaaccatct acccaatact gttacg        26

<210> SEQ ID NO 8
<211> LENGTH: 24
<212> TYPE: DNA
<213> ORGANISM: Artificial Sequence
<220> FEATURE:
<223> OTHER INFORMATION: Target site 5 Rev G17nGG (CD20 gRNA3) Oligo Fw

<400> SEQUENCE: 8
acaccgtatg ctgtaacagt attg        24

<210> SEQ ID NO 9
<211> LENGTH: 24
<212> TYPE: DNA
<213> ORGANISM: Artificial Sequence
<220> FEATURE:
<223> OTHER INFORMATION: Target site 5 Rev G17nGG (CD20 gRNA3) Oligo Rev

<400> SEQUENCE: 9
aaaacaatac tgttacagca tacg        24

<210> SEQ ID NO 10
<211> LENGTH: 25
<212> TYPE: DNA
<213> ORGANISM: Artificial Sequence
<220> FEATURE:
<223> OTHER INFORMATION: Target site 1 Rev G18nGG (CD45.2 gRNA1) Oligo Fw

<400> SEQUENCE: 10
acaccgttgc attttctgaa atcag        25

<210> SEQ ID NO 11
<211> LENGTH: 25
<212> TYPE: DNA
<213> ORGANISM: Artificial Sequence
<220> FEATURE:
<223> OTHER INFORMATION: Target site 1 Rev G18nGG (CD45.2 gRNA1) Oligo Rev

<400> SEQUENCE: 11
aaaactgatt tcagaaaatg caacg        25

<210> SEQ ID NO 12
<211> LENGTH: 26
<212> TYPE: DNA
<213> ORGANISM: Artificial Sequence
<220> FEATURE:
<223> OTHER INFORMATION: Target site 2 Fw G19nGG (CD45.2 gRNA2) Oligo Fw

<400> SEQUENCE: 12
acaccggcta atacttcaat ttgttg        26

<210> SEQ ID NO 13
<211> LENGTH: 26
<212> TYPE: DNA
<213> ORGANISM: Artificial Sequence
<220> FEATURE:
<223> OTHER INFORMATION: Target site 2 Fw G19nGG (CD45.2 gRNA2) Oligo

```
    Rev

<400> SEQUENCE: 13
aaaacaacaa attgaagtat tagccg                                              26
```